US012747480B2

(12) United States Patent
Gauthier et al.

(10) Patent No.: US 12,747,480 B2
(45) Date of Patent: Sep. 29, 2026

(54) METHODS FOR DETERMINATION OF TRANSPLANT REJECTION

(71) Applicant: Natera, Inc., San Carlos, CA (US)

(72) Inventors: Phil Gauthier, Englewood, CO (US); Hossein Tabriziani, San Diego, CA (US); Paul Van Hummelen, San Francisco, CA (US); Jessica Tang, San Jose, CA (US)

(73) Assignee: Natera, Inc., San Carlos, CA (US)

( * ) Notice: Subject to any disclaimer, the term of this patent is extended or adjusted under 35 U.S.C. 154(b) by 382 days.

(21) Appl. No.: 18/282,390

(22) PCT Filed: Mar. 16, 2022

(86) PCT No.: PCT/US2022/020640

§ 371 (c)(1),
(2) Date: Sep. 15, 2023

(87) PCT Pub. No.: WO2022/197864

PCT Pub. Date: Sep. 22, 2022

(65) Prior Publication Data

US 2024/0309472 A1 Sep. 19, 2024

Related U.S. Application Data

(60) Provisional application No. 63/314,647, filed on Feb. 28, 2022, provisional application No. 63/162,750, filed on Mar. 18, 2021.

(51) Int. Cl.

| | |
|---|---|
| ***C12Q 1/6827*** | (2018.01) |
| ***C12Q 1/68*** | (2018.01) |
| ***C12Q 1/6851*** | (2018.01) |
| ***C12Q 1/6858*** | (2018.01) |
| ***C12Q 1/6883*** | (2018.01) |
| ***C12Q 1/70*** | (2006.01) |
| ***G16H 10/40*** | (2018.01) |

(52) U.S. Cl.

CPC ........... *C12Q 1/701* (2013.01); *C12Q 1/6851* (2013.01); *C12Q 1/6883* (2013.01); *C12Q 2600/118* (2013.01); *C12Q 2600/156* (2013.01)

(58) Field of Classification Search

CPC ...... C12Q 1/6806; C12Q 1/6869; C12Q 1/70; G16H 10/40

See application file for complete search history.

(56) References Cited

FOREIGN PATENT DOCUMENTS

| | | | |
|---|---|---|---|
| EP | 2653562 | A1 | 10/2013 |
| WO | WO-2015070086 | A1 | 5/2015 |
| WO | WO-2020010255 | A1 | 1/2020 |

OTHER PUBLICATIONS

Burnham P., et al., "Single-Stranded DNA Library Preparation Uncovers the Origin and Diversity of Ultrashort Cell-Free DNA in Plasma," Scientific Reports, Jun. 14, 2016, vol. 6, No. 27859, 9 Pages.

Grenda R., "Torque Teno (TTV) Viral Load as a Biomarker of Immunosuppressive Strength after Kidney Transplantation in Children," Pediatric Nephrology, Jan. 2021, vol. 36, No. 1, , pp. 1-3, DOI: 10.1007/S00467-020-04607-2, ISSN: 0931-041X, XP037316360. (The whole document abstract, p. 2, col. 1).

International Preliminary Report on Patentability for International Application No. PCT/US2022/020640, mailed Sep. 28, 2023, 10 Pages.

International Search Report and Written Opinion for International Application No. PCT/US2022/020640, mailed Jun. 29, 2022, 14 Pages.

Kulifaj D., et al., "Development of a Standardized Real Time PCR for Torque Teno Viruses (TTV) Viral Load Detection and Quantification: A New Tool for Immune monitoring," Journal of Clinical Virology, 2018, vol. 105, pp. 118-127.

*Primary Examiner* — Barry A Chestnut

(57) ABSTRACT

The present disclosure provides methods for preparation and analysis of biological samples of transplant recipients for determination of transplant rejection, comprising: (a) measuring the amount of *Torque teno* virus (TTV) in a blood, plasma, serum, or urine sample of a transplant recipient; (b) measuring the amount of donor-derived cell-free DNA in a blood, plasma, serum, or urine sample of the transplant recipient; and (c) determining whether the amount of donor-derived cell-free DNA or a function thereof exceeds a cutoff threshold indicating transplant rejection and whether the transplant recipient has an increased or decreased amount of TTV indicating decreased or increased immune response, respectively.

18 Claims, 3 Drawing Sheets

METHODS FOR DETERMINATION OF TRANSPLANT REJECTION

CROSS-REFERENCE TO RELATED APPLICATIONS

This application claims the benefit of U.S. Provisional Application Ser. No. 63/162,750, filed Mar. 18, 2019 and U.S. Provisional Application Ser. No. 63/314,647, filed Feb. 28, 2022, which are hereby incorporated by reference in their entirety.

BACKGROUND

Rapid detection of graft injury and/or rejection remains a challenge for transplant recipients. Conventional biopsy-based tests are invasive and costly and possibly lead to late diagnosis of transplant injury and/or rejection. Therefore, there is a need for a non-invasive test for transplant injury and/or rejection that is more sensitive and more specific than conventional biopsy-based tests.

SUMMARY

The present disclosure relates to preparation and analysis of biological samples of transplant recipients for determination of transplant rejection, comprising: (a) measuring the amount of *Torque teno* virus (TTV) in a blood, plasma, serum, or urine sample of a transplant recipient; (b) measuring the amount of donor-derived cell-free DNA in a blood, plasma, serum, or urine sample of the transplant recipient; and (c) determining whether the amount of donor-derived cell-free DNA or a function thereof exceeds a cutoff threshold indicating transplant rejection and whether the transplant recipient has an increased or decreased amount of TTV indicating decreased or increased immune response, respectively.

The present disclosure also relates to preparation and analysis of biological samples of transplant recipients for determination of transplant rejection, comprising: measuring the amount of *Torque teno* virus (TTV) and the amount of donor-derived cell-free DNA in a blood, plasma, serum, or urine sample of a transplant recipient; and determining whether a combination of the amount of donor-derived cell-free DNA or a function thereof (as a marker of organ health) and the amount of TTV of a function thereof (as a marker of immunosuppression) exceeds a cutoff threshold indicating transplant rejection. The combination of TTV and dd-cfDNA can serve as a biomarker for rejection and as a biomarker for net state of immunosuppression.

The present disclosure further relates to preparation and analysis of biological samples of transplant recipients for determination of transplant rejection, comprising: (a) measuring the amount of TTV DNA in a blood, plasma, serum, or urine sample of a transplant recipient; (b) measuring the amount of donor-derived cell-free DNA in a blood, plasma, serum, or urine sample of the transplant recipient and/or the percentage of donor-derived cell-free DNA out of total cell-free DNA; and (c) determining the rejection risk for the transplant recipient based on the amount of donor-derived cell-free DNA and/or the percentage of donor-derived cell-free DNA out of total cell-free DNA, and the amount of TTV DNA in the blood, plasma, serum, or urine sample of the transplant recipient.

DETAILED DESCRIPTION

Figure 1:
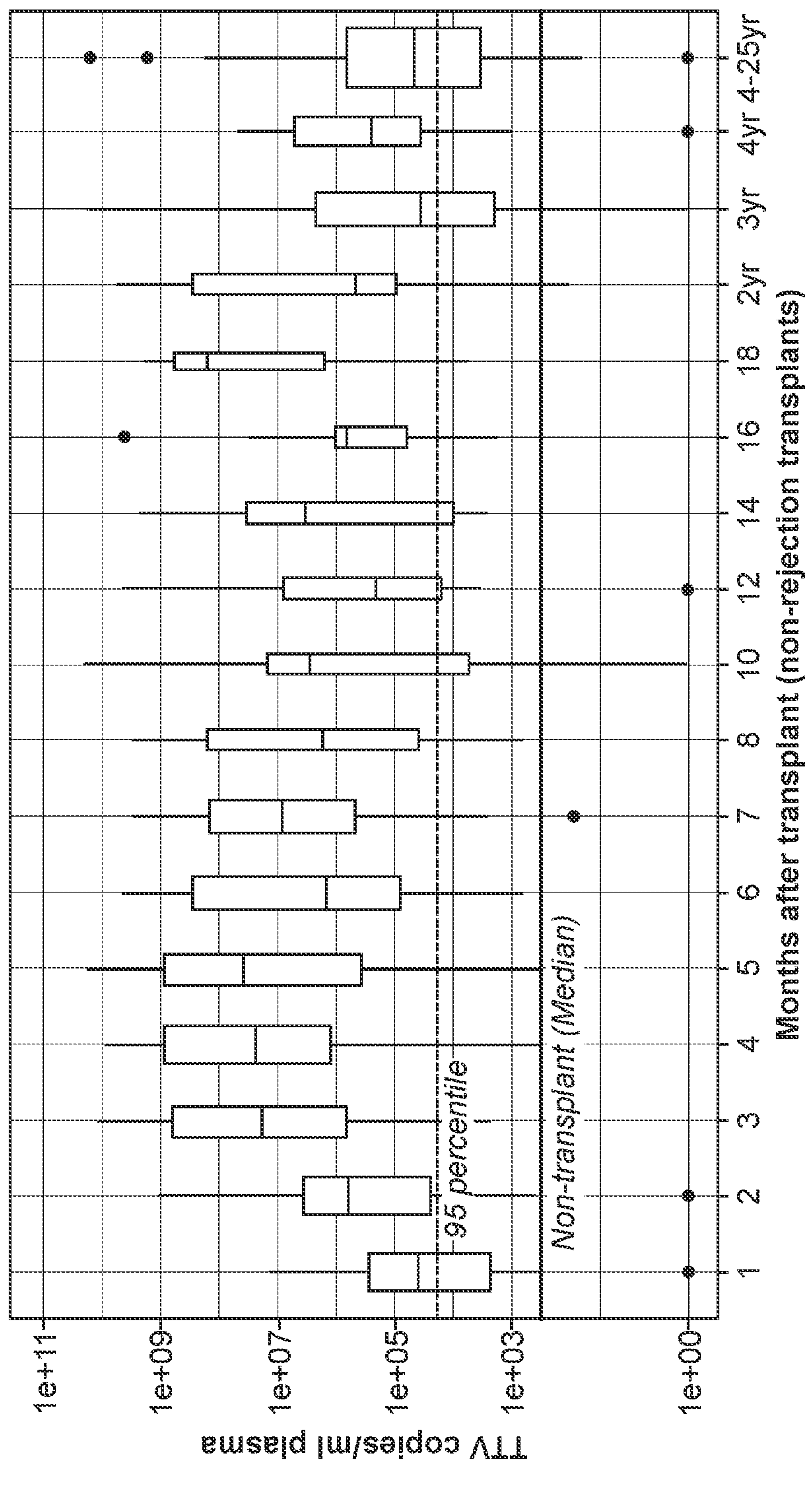
FIG. 1. TTV titer Log (cps/mL) reaches peak at month 3 post-transplantation. All torque teno virus (TTV) measurements (n=516) are included. TTV load is displayed in box plots, where lower whisker=smallest observation greater than or equal to lower hinge−1.5*IQR; lower hinge, 25% quantile; middle, median, 50% quantile; upper hinge, 75% quantile; upper whisker=largest observation less than or equal to upper hinge+1.5*IQR. The blue horizontal line represents the median TTV titer of healthy control plasma samples (n=56) and the 95th percentile as dotted line.

Sigdel et al., "Optimizing Detection of Kidney Transplant Injury by Assessment of Donor-Derived Cell-Free DNA via Massively Multiplex PCR." *J. Clin. Med.* 8(1):19 (2019), is incorporated herein by reference in its entirety.

WO2020/010255, titled "Methods for Detection of Donor-Derived Cell-Free DNA" and filed on Jul. 3, 2019 as PCT/US2019/040603, is incorporated herein by reference in its entirety.

U.S. Prov. Appl. No. 63/031,879, titled "Improved Methods for Detection of Donor Derived Cell-Free DNA" and filed on May 29, 2020, is incorporated herein by reference in its entirety.

In at least one aspect, the present invention relates to a method of preparing a composition of amplified DNA derived from a blood, plasma, serum or urine sample of a transplant recipient useful for determination of transplant rejection, comprising: (a) extracting cell-free DNA from the blood, plasma, serum or urine sample of the transplant recipient, wherein the extracted cell-free DNA comprises donor-derived cell-free DNA and recipient-derived cell-free DNA; (b) preparing a composition of amplified DNA by performing targeted amplification of the extracted DNA at 200-50,000 target loci in a single reaction volume, and sequencing the amplified DNA by high-throughput sequencing to obtain sequencing reads and quantifying the amount of donor-derived cell-free DNA based on the sequencing reads; (c) measuring the amount of *Torque teno* virus (TTV) in a blood, plasma, serum, or urine sample of the transplant recipient; and (d) determining whether the amount of donor-derived cell-free DNA or a function thereof exceeds a cutoff threshold indicating transplant rejection and whether the transplant recipient has an increased or decreased amount of TTV indicating decreased or increased immune response, respectively.

In at least one aspect, the present invention relates to a method of preparing a composition of amplified DNA derived from a blood, plasma, serum or urine sample of a transplant recipient useful for determination of transplant rejection, comprising: (a) extracting cell-free DNA from the blood, plasma, serum or urine sample of the transplant recipient, wherein the extracted cell-free DNA comprises donor-derived cell-free DNA and recipient-derived cell-free DNA; (b) preparing a composition of amplified DNA by performing targeted amplification of the extracted DNA at 200-50,000 target loci in a single reaction volume, and sequencing the amplified DNA by high-throughput sequencing to obtain sequencing reads and quantifying the amount of donor-derived cell-free DNA and the amount of *Torque teno* virus (TTV) based on the sequencing reads; and (c) determining whether a combination of the amount of donor-derived cell-free DNA or a function thereof (as a marker of organ health) and the amount of TTV of a function thereof (as a marker of immunosuppression) exceeds a cutoff threshold. The combination of TTV and dd-cfDNA can serve as a biomarker for rejection and as a biomarker for net state of immunosuppression.

In at least another aspect, the present invention relates to a method of preparing a composition of amplified DNA derived from a blood, plasma, serum or urine sample of a transplant recipient useful for determination of transplant rejection, comprising: (a) extracting cell-free DNA from the blood, plasma, serum or urine sample of the transplant recipient, wherein the extracted cell-free DNA comprises donor-derived cell-free DNA and recipient-derived cell-free DNA; (b) preparing a composition of amplified DNA by performing targeted amplification of the extracted DNA at 200-50,000 target loci in a single reaction volume, and sequencing the amplified DNA by high-throughput sequencing to obtain sequencing reads and quantifying the amount of donor-derived cell-free DNA in the blood, plasma, serum, or urine sample and/or the percentage of donor-derived cell-free DNA out of total cell-free DNA based on the sequencing reads; (c) measuring the amount of TTV DNA in the blood, plasma, serum, or urine sample of the transplant recipient; and (d) determining the rejection risk for the transplant recipient based on the amount of donor-derived cell-free DNA and/or the percentage of donor-derived cell-free DNA out of total cell-free DNA, and the amount of TTV DNA in the blood, plasma, serum, or urine sample of the transplant recipient.

In at least another aspect, the present invention relates to a method of preparing a composition of amplified DNA derived from a blood, plasma, serum or urine sample of a transplant recipient useful for determination of transplant rejection, comprising: (a) extracting cell-free DNA from the blood, plasma, serum or urine sample of the transplant recipient, wherein the extracted cell-free DNA comprises donor-derived cell-free DNA and recipient-derived cell-free DNA; (b) preparing a composition of amplified DNA by performing targeted amplification of the extracted DNA at 200-50,000 target loci in a single reaction volume, and sequencing the amplified DNA by high-throughput sequencing to obtain sequencing reads and quantifying the amount of donor-derived cell-free DNA in the blood, plasma, serum, or urine sample and/or the estimated percentage of donor-derived cell-free DNA out of total cell-free DNA, and the amount of TTV DNA in the blood, plasma, serum, or urine sample, based on the sequencing reads; and (c) determining the rejection risk for the transplant recipient based on the amount of donor-derived cell-free DNA and/or the percentage of donor-derived cell-free DNA out of total cell-free DNA, and the amount of TTV DNA in the blood, plasma, serum, or urine sample of the transplant recipient.

In some embodiments, the dd-cfDNA assay result is compared to a cutoff threshold to determine the occurrence or likely occurrence of transplant rejection, wherein the cutoff threshold is a function of the amount of donor-derived cell-free DNA and the amount of TTV. In some embodiments, the dd-cfDNA assay result is compared to a cutoff threshold to determine the occurrence or likely occurrence of transplant rejection, wherein the cutoff threshold is a function of the amount of donor-derived cell-free DNA, the amount of TTV, and the amount of total cell-free DNA. In some embodiments, the dd-cfDNA assay result is compared to a cutoff threshold to determine the occurrence or likely occurrence of transplant rejection, wherein the cutoff threshold is a function of the number of reads of donor-derived cell-free DNA and the number of reads of TTV. In some embodiments, the dd-cfDNA assay result is compared to a cutoff threshold to determine the occurrence or likely occurrence of transplant rejection, wherein the cutoff threshold is a function of the number of reads of donor-derived cell-free DNA, the number of reads of TTV, and the number of reads of total cell-free DNA. In some embodiments, the function is a polynomial function. In some embodiments, the function is a logarithm function. In some embodiments, the function is an exponential function. In some embodiments, the function is a linear function. In some embodiments, the function is a nonlinear function.

In some embodiments, wherein the rejection risk for the transplant recipient is determined using logistic regression, random forest, or decision tree machine learning analysis. In some embodiments, the machine learning analysis incorporates the amount of donor-derived cell-free DNA in the blood, plasma, serum, or urine sample of the transplant recipient or a function thereof as a parameter. In some embodiments, the machine learning analysis incorporates the number of reads of donor-derived cell-free DNA or a function thereof as a parameter. In some embodiments, the machine learning analysis incorporates the estimated percentage of donor-derived cell-free DNA out of total cell-free DNA as a parameter. In some embodiments, the machine learning analysis incorporates the amount of TTV DNA in the blood, plasma, serum, or urine sample of the transplant recipient as a parameter. In some embodiments, the machine learning analysis further incorporates the amount of total cell-free DNA in the blood, plasma, serum, or urine sample of the transplant recipient or a function thereof as a parameter. In some embodiments, the machine learning analysis further incorporates the number of reads of total cell-free DNA or a function thereof as a parameter. In some embodiments, the machine learning analysis further incorporates time post-transplantation as a parameter. In some embodiments, the machine learning analysis further incorporates the age of transplant recipient and/or transplant donor as a parameter. In some embodiments, the machine learning analysis further incorporates the gender of transplant recipient and/or transplant donor as a parameter.

In some embodiments, the blood, plasma, serum or urine sample is obtained from the transplant recipient less than 18 months post-transplantation, less than 17 months post-transplantation, less than 16 months post-transplantation, less than 15 months post-transplantation, less than 14 months post-transplantation, less than 13 months post-transplantation, or less than 12 months post-transplantation. In some embodiments, the blood, plasma, serum or urine sample is obtained from the transplant recipient between 0 and 2 months post-transplantation, between 2 and 4 months post-transplantation, between 4 and 6 months post-transplantation, between 6 and 9 months post-transplantation, between 9 and 12 months post-transplantation, or between 12 and 18 months post-transplantation.

In some embodiments, the rejection risk for the transplant recipient is determined with a sensitivity of at least 0.81, or at least 0.82, or at least 0.83, or at least 0.84, or at least 0.85, or at least 0.86, or at least 0.87, or at least 0.88, or at least 0.89, or at least 0.90. In some embodiments, the rejection risk for the transplant recipient is determined with a specificity of at least 0.81, or at least 0.82, or at least 0.83, or at least 0.84, or at least 0.85, or at least 0.86, or at least 0.87, or at least 0.88, or at least 0.89, or at least 0.90. In some embodiments, the rejection risk for the transplant recipient is determined with an area under the curve (AUC) of at least at least 0.86, or at least 0.87, or at least 0.88, or at least 0.89, or at least 0.90, or at least 0.91 or at least 0.92, or at least 0.93, or at least 0.94, or at least 0.95.

In some embodiments, the TTV is *Torque teno* virus 1. In some embodiments, the TTV is *Torque teno* virus 2. In some embodiments, the TTV is *Torque teno* virus 3. In some embodiments, the TTV is *Torque teno* virus 4. In some embodiments, the TTV is *Torque teno* virus 5. In some embodiments, the TTV is *Torque teno* virus 6. In some embodiments, the TTV is *Torque teno* virus 7. In some embodiments, the TTV is *Torque teno* virus 9. In some embodiments, the TTV is *Torque teno* virus 10. In some embodiments, the TTV is *Torque teno* virus 13. In some embodiments, the TTV is *Torque teno* virus 14. In some embodiments, the TTV is *Torque teno* virus 15. In some embodiments, the TTV is *Torque teno* virus 17. In some embodiments, the TTV is *Torque teno* virus 18. In some embodiments, the TTV is *Torque teno* virus 19. In some embodiments, the TTV is *Torque teno* virus 20. In some embodiments, the TTV is *Torque teno* virus 21. In some embodiments, the TTV is *Torque teno* virus 24. In some embodiments, the TTV is *Torque teno* virus 25. In some embodiments, the TTV is *Torque teno* virus 26. In some embodiments, the TTV is *Torque teno* virus 29. In some embodiments, the TTV is *Torque teno* virus 31. In some embodiments, an decreased amount of TTV indicates increased immune response or increased immune activity in the transplant recipient. In some embodiments, an increased amount of TTV indicates decreased immune response or decreased immune activity in the transplant recipient.

In some embodiments, the amount of TTV is measured by quantitative PCR. In some embodiments, the amount of TTV is measured by real-time PCR. In some embodiments, the amount of TTV is measured by digital PCR. In some embodiments, the amount of TTV is measured by sequencing such as high-throughput sequencing, next-generation sequence, or sequencing-by-synthesis.

In some embodiments, the transplant donor is a human subject. In some embodiments, the transplant donor is a non-human mammalian subject (e.g., pig). In some embodiments, the transplant recipient is a human subject.

In some embodiments, the transplant recipient has received one or more transplanted organs selected from kidney, liver, heart, lung, pancreas, intestinal, thymus, and uterus. In some embodiments, the transplant recipient has received a kidney transplant. In some embodiments, the transplant recipient has received a liver transplant. In some embodiments, the transplant recipient has received a heart transplant. In some embodiments, the transplant recipient has received a lung transplant. In some embodiments, the transplant recipient has received a pancreas transplant. In some embodiments, the transplant recipient has received an intestinal transplant. In some embodiments, the transplant recipient has received a thymus transplant. In some embodiments, the transplant recipient has received a uterus transplant.

In some embodiments, the target loci comprise single nucleotide polymorphism (SNP) loci.

In some embodiments, the targeted amplification comprises PCR. In some embodiments, the primers for the targeted amplification include 200-50,000, 500-20,000, or 1,000-10,000, or 200-500, or 500-1,000, or 1,000-2,000, or 2,000-5,000, or 5,000-10,000, or 10,000-20,000, or 20,000-50,000 pairs of forward and reverse PCR primers. In some embodiments, the targeted amplification comprises performing amplification at 500-20,000, or 1,000-10,000, or 200-500, or 500-1,000, or 1,000-2,000, or 2,000-5,000, or 5,000-10,000, or 10,000-20,000, or 20,000-50,000 target loci in a single reaction volume using 500-20,000, or 1,000-10,000, or 200-500, or 500-1,000, or 1,000-2,000, or 2,000-5,000, or 5,000-10,000, or 10,000-20,000, or 20,000-50,000 primer pairs to obtain amplification products.

In some embodiments, the targeted amplification comprises nested PCR. In some embodiments, the primers for the targeted amplification include a first universal primer and 200-50,000, 500-20,000, or 1,000-10,000, or 200-500, or 500-1,000, or 1,000-2,000, or 2,000-5,000, or 5,000-10,000, or 10,000-20,000, or 20,000-50,000 target-specific primers, and a second universal primer and 200-50,000, 500-20,000, or 1,000-10,000, or 200-500, or 500-1,000, or 1,000-2,000, or 2,000-5,000, or 5,000-10,000, or 10,000-20,000, or 20,000-50,000 inner target-specific primers. In some embodiments, the targeted amplification comprises performing amplification at 500-20,000, or 1,000-10,000, or 200-500, or 500-1,000, or 1,000-2,000, or 2,000-5,000, or 5,000-10,000, or 10,000-20,000, or 20,000-50,000 target loci in a single reaction volume using a first universal primer and 200-50,000, 500-20,000, or 1,000-10,000, or 200-500, or 500-1,000, or 1,000-2,000, or 2,000-5,000, or 5,000-10,000, or 10,000-20,000, or 20,000-50,000 target-specific primers to obtain amplification products. In some embodiments, the targeted amplification comprises performing amplification at 500-20,000, or 1,000-10,000, or 200-500, or 500-1,000, or 1,000-2,000, or 2,000-5,000, or 5,000-10,000, or 10,000-20,000, or 20,000-50,000 target loci in a single reaction volume using a second universal primer and 200-50,000, 500-20,000, or 1,000-10,000, or 200-500, or 500-1,000, or 1,000-2,000, or 2,000-5,000, or 5,000-10,000, or 10,000-20,000, or 20,000-50,000 inner target-specific primers to obtain amplification products.

In some embodiments, the cutoff threshold is an estimate percentage of donor-derived cell-free DNA out of total cell-free DNA or a function thereof. In some embodiments, the cutoff threshold is 1.0%, 1.1%, 1.2%, 1.3%, 1.4%, 1.5%, 1.6%, 1.7%, 1.8%, 1.9%, or 2.0% dd-cfDNA. In some embodiments, the cutoff threshold is adjusted according to the type of organs transplanted. In some embodiments, the cutoff threshold is adjusted according to the number of organs transplanted.

In some embodiments, the cutoff threshold is proportional to an absolute donor-derived cell-free DNA concentration. In some embodiments, the cutoff threshold is a copy number of donor-derived cell-free DNA or a function thereof. In some embodiments, the cutoff threshold is expressed as quantity or absolute quantity of dd-cfDNA. In some embodiments, the cutoff threshold is expressed as quantity or absolute quantity of dd-cfDNA per volume unit of the blood sample. In some embodiments, the cutoff threshold is expressed as quantity or absolute quantity of dd-cfDNA per volume unit of the blood sample multiplied by body mass, BMI, or blood volume of the transplant recipient.

In some embodiments, the method further comprises attaching tags to the amplification products prior to performing high-throughput sequencing, wherein the tags comprise sequencing-compatible adaptors. In some embodiments, the method further comprises attaching tags to the extracted cell-free DNA prior to performing targeted amplification, wherein the tags comprise adaptors for amplification. In some embodiment, the tags comprise sample-specific barcodes, and wherein the method further comprises pooling the amplification products from a plurality of samples prior to high-throughput sequencing and sequencing the pool of amplification products together in a single run during the high-throughput sequencing.

In some embodiments, the method further comprises repeating steps (a)-(d) longitudinally for the same transplant recipient, and determining a longitudinal change in the amount of TTV or a function thereof and a longitudinal change in the amount of donor-derived cell-free DNA or a function thereof.

In at least another aspect, the present invention relates to a method of administrating immunosuppressive therapy in a transplant recipient, comprising: (a) measuring the amount of *Torque teno* virus (TTV) in a blood, plasma, serum, or urine sample of the transplant recipient; and (b) measuring the amount of donor-derived cell-free DNA in a blood, plasma, serum, or urine sample of the transplant recipient; and (c) titrating the dosage of an immunosuppressive therapy according to the amount of TTV or a function thereof and the amount of donor-derived cell-free DNA or a function thereof.

In some embodiments, the method further comprises repeating steps (a)-(b) longitudinally for the same transplant recipient, and determining a longitudinal change in the amount of TTV or a function thereof and a longitudinal change in the amount of donor-derived cell-free DNA or a function thereof.

In some embodiments, the method further comprises titrating the dosage of the immunosuppressive therapy according to the longitudinal change in the amount of TTV or a function thereof and the longitudinal change in the amount of donor-derived cell-free DNA or a function thereof.

In some embodiments, the method comprises increasing the dosage of immunosuppressive therapy if the transplant recipient has a longitudinally decreased amount of TTV and a longitudinally increased amount of donor-derived cell-free DNA.

In some embodiments, the method comprises decreasing the dosage of immunosuppressive therapy if the transplant recipient has a longitudinally increased amount of TTV and a longitudinally decreased amount of donor-derived cell-free DNA.

In some embodiments, the amount of donor-derived cell-free DNA is measured by: extracting cell-free DNA from the blood, plasma, serum or urine sample of the transplant recipient, wherein the extracted cell-free DNA comprises donor-derived cell-free DNA and recipient-derived cell-free DNA; performing targeted amplification of the extracted DNA at 200-50,000 target loci in a single reaction volume; sequencing the amplified DNA by high-throughput sequencing to obtain sequencing reads and quantifying the amount of donor-derived cell-free DNA based on the sequencing reads.

In some embodiments, the method is performed without prior knowledge of donor genotypes. In some embodiments, the method does not comprise genotyping transplant donor (s).

In some embodiments, for example, tracer DNA, or internal calibration DNA, refers to a composition of DNA for which one or more of the following is known advance-length, sequence, nucleotide composition, quantity, or biological origin. The tracer DNA can be added to a biological sample derived from a human subject to help estimate the amount of total cfDNA in said sample. It can also be added to reaction mixtures other than the biological sample itself.

In some embodiments, for example, single nucleotide polymorphism (SNP) refers to a single nucleotide that may differ between the genomes of two members of the same species. The usage of the term does not imply any limit on the frequency with which each variant occurs.

In some embodiments, for example, sequence refers to a DNA or RNA sequence or a genetic sequence. It may refer to the primary, physical structure of the DNA or RNA molecule or strand in an individual. It may refer to the sequence of nucleotides found in that DNA or RNA molecule, or the complementary strand to the DNA or RNA molecule. It may refer to the information contained in the DNA or RNA molecule as its representation in silico.

In some embodiments, for example, locus refers to a particular region of interest on the DNA or RNA of an individual and includes without limitation one or more SNPs, the site of a possible insertion or deletion, or the site of some other relevant genetic variation. Disease-linked SNPs may also refer to disease-linked loci.

In some embodiments, for example, polymorphic allele, also "polymorphic locus," refers to an allele or locus where the genotype varies between individuals within a given species. Some examples of polymorphic alleles include single nucleotide polymorphisms (SNPs), short tandem repeats, deletions, duplications, and inversions.

In some embodiments, for example, allele refers to the nucleotides or nucleotide sequence occupying a particular locus.

In some embodiments, for example, genetic data also "genotypic data" refers to the data describing aspects of the genome of one or more individuals. It may refer to one or a set of loci, partial or entire sequences, partial or entire chromosomes, or the entire genome. It may refer to the identity of one or a plurality of nucleotides; it may refer to a set of sequential nucleotides, or nucleotides from different locations in the genome, or a combination thereof. Genotypic data is typically in silico, however, it is also possible to consider physical nucleotides in a sequence as chemically encoded genetic data. Genotypic Data may be said to be "on," "of," "at," "from" or "on" the individual(s). Genotypic Data may refer to output measurements from a genotyping platform where those measurements are made on genetic material.

In some embodiments, for example, genetic material also "genetic sample" refers to physical matter, such as tissue or blood, from one or more individuals comprising nucleic acids (e.g., comprising DNA or RNA)

In some embodiments, for example, allelic data refers to a set of genotypic data concerning a set of one or more alleles. It may refer to the phased, haplotypic data. It may refer to SNP identities, and it may refer to the sequence data of the nucleic acid, including insertions, deletions, repeats and mutations.

In some embodiments, for example, allelic state refers to the actual state of the genes in a set of one or more alleles. It may refer to the actual state of the genes described by the allelic data.

In some embodiments, for example, allelic ratio or allele ratio, refers to the ratio between the amount of each allele at a locus that is present in a sample or in an individual. When the sample was measured by sequencing, the allelic ratio may refer to the ratio of sequence reads that map to each allele at the locus. When the sample was measured by an intensity based measurement method, the allele ratio may refer to the ratio of the amounts of each allele present at that locus as estimated by the measurement method.

In some embodiments, for example, allele count refers to the number of sequences that map to a particular locus, and if that locus is polymorphic, it refers to the number of sequences that map to each of the alleles. If each allele is counted in a binary fashion, then the allele count will be whole number. If the alleles are counted probabilistically, then the allele count can be a fractional number.

In some embodiments, for example, primer, also “PCR probe” refers to a single DNA molecule (a DNA oligomer) or a collection of DNA molecules (DNA oligomers) where the DNA molecules are identical, or nearly so, and where the primer contains a region that is designed to hybridize to a targeted polymorphic locus, and contain a priming sequence designed to allow amplification such as PCR amplification. A primer may also contain a molecular barcode. A primer may contain a random region that differs for each individual molecule.

In some embodiments, for example, hybrid capture probe refers to any nucleic acid sequence, possibly modified, that is generated by various methods such as PCR or direct synthesis and intended to be complementary to one strand of a specific target DNA or RNA sequence in a sample. The exogenous hybrid capture probes may be added to a prepared sample and hybridized through a denaturation-reannealing process to form duplexes of exogenous-endogenous fragments. These duplexes may then be physically separated from the sample by various means.

In some embodiments, for example, sequence read refers to data representing a sequence of nucleotide bases that were measured using a clonal sequencing method. Clonal sequencing may produce sequence data representing single, or clones, or clusters of one original DNA or RNA molecule. A sequence read may also have associated quality score at each base position of the sequence indicating the probability that nucleotide has been called correctly.

In some embodiments, for example, mapping a sequence read is the process of determining a sequence read's location of origin in the genome sequence of a particular organism. The location of origin of sequence reads is based on similarity of nucleotide sequence of the read and the genome sequence.

In some embodiments, for example, DNA or RNA of donor origin refers to DNA or RNA that was originally part of a cell whose genotype was essentially equivalent to that of the transplant donor. The donor can be a human or a non-human mammalian (e.g., pig).

In some embodiments, for example, DNA or RNA of recipient origin refers to DNA or RNA that was originally part of a cell whose genotype was essentially equivalent to that of the transplant recipient.

In some embodiments, for example, transplant recipient plasma refers to the plasma portion of the blood from a female from a patient who has received an allograft or xenograft, e.g., an organ transplant recipient.

In some embodiments, for example, preferential enrichment of DNA or RNA that corresponds to a locus, or preferential enrichment of DNA or RNA at a locus, refers to any technique that results in the percentage of molecules of DNA or RNA in a post-enrichment DNA or RNA mixture that correspond to the locus being higher than the percentage of molecules of DNA or RNA in the pre-enrichment DNA or RNA mixture that correspond to the locus. The technique may involve selective amplification of DNA or RNA molecules that correspond to a locus. The technique may involve removing DNA or RNA molecules that do not correspond to the locus. The technique may involve a combination of methods. The degree of enrichment is defined as the percentage of molecules of DNA or RNA in the post-enrichment mixture that correspond to the locus divided by the percentage of molecules of DNA or RNA in the pre-enrichment mixture that correspond to the locus. Preferential enrichment may be carried out at a plurality of loci. In some embodiments of the present disclosure, the degree of enrichment is greater than 20. In some embodiments of the present disclosure, the degree of enrichment is greater than 200. In some embodiments of the present disclosure, the degree of enrichment is greater than 2,000. When preferential enrichment is carried out at a plurality of loci, the degree of enrichment may refer to the average degree of enrichment of all of the loci in the set of loci.

In some embodiments, for example, amplification refers to a technique that increases the number of copies of a molecule of DNA or RNA.

In some embodiments, for example, selective amplification may refer to a technique that increases the number of copies of a particular molecule of DNA or RNA, or molecules of DNA or RNA that correspond to a particular region of DNA or RNA. It may also refer to a technique that increases the number of copies of a particular targeted molecule of DNA or RNA, or targeted region of DNA or RNA more than it increases non-targeted molecules or regions of DNA or RNA. Selective amplification may be a method of preferential enrichment.

In some embodiments, for example, universal priming sequence refers to a DNA sequence that may be appended to a population of target DNA molecules, for example by ligation, PCR, or ligation mediated PCR. Once added to the population of target molecules, primers specific to the universal priming sequences can be used to amplify the target population using a single pair of amplification primers. Universal priming sequences need not be related to the target sequences.

In some embodiments, for example, universal adapters, or ‘ligation adaptors’ or ‘library tags’ are DNA molecules containing a universal priming sequence that can be covalently linked to the 5-prime and 3-prime end of a population of target double stranded DNA molecules. The addition of the adapters provides universal priming sequences to the 5-prime and 3-prime end of the target population from which PCR amplification can take place, amplifying all molecules from the target population, using a single pair of amplification primers.

In some embodiments, for example, targeting refers to a method used to selectively amplify or otherwise preferentially enrich those molecules of DNA or RNA that correspond to a set of loci in a mixture of DNA or RNA.

Analysis of Donor-Derived Cell-Free DNA for Monitoring Transplant Rejection

In one aspect, the present invention relates to a method of quantifying the amount of donor-derived cell-free DNA (dd-cfDNA) in a blood sample of a transplant recipient, comprising: extracting DNA from the blood sample of the transplant recipient, wherein the DNA comprises donor-derived cell-free DNA and recipient-derived cell-free DNA; performing targeted amplification at 500-50,000 target loci in a single reaction volume using 500-50,000 primer pairs, wherein the target loci comprise polymorphic loci and non-polymorphic loci, and wherein each primer pair is designed to amplify a target sequence of no more than 100 bp; and quantifying the amount of donor-derived cell-free DNA in the amplification products.

In another aspect, the present invention relates to a method of quantifying the amount of donor-derived cell-free DNA (dd-cfDNA) in a blood sample of a transplant recipient, comprising: extracting DNA from the blood sample of the transplant recipient, wherein the DNA comprises donor-derived cell-free DNA and recipient-derived cell-free DNA, and wherein the extracting step comprises size selection to enrich for donor-derived cell-free DNA and reduce the amount of recipient-derived cell-free DNA disposed from bursting white-blood cells; performing targeted amplification at 500-50,000 target loci in a single reaction volume using 500-50,000 primer pairs, wherein the target loci comprise polymorphic loci and non-polymorphic loci; and quantifying the amount of donor-derived cell-free DNA in the amplification products.

In another aspect, the present invention relates to a method of detecting donor-derived cell-free DNA (dd-cfDNA) in a blood sample of a transplant recipient, comprising: extracting DNA from the blood sample of the transplant recipient, wherein the DNA comprises donor-derived cell-free DNA and recipient-derived cell-free DNA; performing targeted amplification at 500-50,000 target loci in a single reaction volume using 500-50,000 primer pairs, wherein the target loci comprise polymorphic loci and non-polymorphic loci; sequencing the amplification products by high-throughput sequencing; and quantifying the amount of donor-derived cell-free DNA.

In some embodiments, the method further comprises performing universal amplification of the extracted DNA. In some embodiments, the universal amplification preferentially amplifies donor-derived cell-free DNA over recipient-derived cell-free DNA that are disposed from bursting white-blood cells.

In some embodiments, the transplant recipient is a mammal. In some embodiments, the transplant recipient is a human.

In some embodiments, the transplant recipient has received a transplant selected from organ transplant, tissue transplant, cell transplant, and fluid transplant. In some embodiments, the transplant recipient has received a transplant selected from kidney transplant, liver transplant, pancreas transplant, intestinal transplant, heart transplant, lung transplant, heart/lung transplant, stomach transplant, testis transplant, penis transplant, ovary transplant, uterus transplant, thymus transplant, face transplant, hand transplant, leg transplant, bone transplant, bone marrow transplant, cornea transplant, skin transplant, pancreas islet cell transplant, heart valve transplant, blood vessel transplant, and blood transfusion. In some embodiments, the transplant recipient has received SPK transplant.

In some embodiments, the quantifying step comprises determining the percentage of donor-derived cell-free DNA out of the total of donor-derived cell-free DNA and recipient-derived cell-free DNA in the blood sample. In some embodiments, the quantifying step comprises determining the number of copies of donor-derived cell-free DNA per volume unit of the blood sample.

In some embodiments, the method further comprises detecting the occurrence or likely occurrence of active rejection of transplantation using the quantified amount of donor-derived cell-free DNA. In some embodiments, the method is performed without prior knowledge of donor genotypes.

In some embodiments, each primer pair is designed to amplify a target sequence of about 50-100 bp. In some embodiments, each primer pair is designed to amplify a target sequence of no more than 75 bp. In some embodiments, each primer pair is designed to amplify a target sequence of about 60-75 bp. In some embodiments, each primer pair is designed to amplify a target sequence of about 65 bp.

In some embodiments, the targeted amplification comprises amplifying at least 1,000 polymorphic loci in a single reaction volume. In some embodiments, the targeted amplification comprises amplifying at least 2,000 polymorphic loci in a single reaction volume. In some embodiments, the targeted amplification comprises amplifying at least 5,000 polymorphic loci in a single reaction volume. In some embodiments, the targeted amplification comprises amplifying at least 10,000 polymorphic loci in a single reaction volume.

In some embodiments, method further comprises measuring an amount of one or more alleles at the target loci that are polymorphic loci. In some embodiments, the polymorphic loci and the non-polymorphic loci are amplified in a single reaction.

In some embodiments, the quantifying step comprises detecting the amplified target loci using a microarray. In some embodiments, the quantifying step does not comprise using a microarray.

In some embodiments, the targeted amplification comprises simultaneously amplifying 500-50,000 target loci in a single reaction volume using (i) at least 500-50,000 different primer pairs, or (ii) at least 500-50,000 target-specific primers and a universal or tag-specific primer 500-50,000 primer pairs.

In a further aspect, the present invention relates to a method of determining the likelihood of transplant rejection within a transplant recipient, the method comprising: extracting DNA from the blood sample of the transplant recipient, wherein the DNA comprises donor-derived cell-free DNA and recipient-derived cell-free DNA; performing universal amplification of the extracted DNA; performing targeted amplification at 500-50,000 target loci in a single reaction volume using 500-50,000 primer pairs, wherein the target loci comprise polymorphic loci and non-polymorphic loci; sequencing the amplification products by high-throughput sequencing; and quantifying the amount of donor-derived cell-free DNA in the blood sample, wherein a greater amount of dd-cfDNA indicates a greater likelihood of transplant rejection.

In a further aspect, the present invention relates to a method of diagnosing a transplant within a transplant recipient as undergoing acute rejection, the method comprising: extracting DNA from the blood sample of the transplant recipient, wherein the DNA comprises donor-derived cell-free DNA and recipient-derived cell-free DNA; performing universal amplification of the extracted DNA; performing targeted amplification at 500-50,000 target loci in a single reaction volume using 500-50,000 primer pairs, wherein the target loci comprise polymorphic loci and non-polymorphic loci; sequencing the amplification products by high-throughput sequencing; and quantifying the amount of donor-derived cell-free DNA in the blood sample, wherein an amount of dd-cfDNA of greater than 1% (or 1.1%, or 1.2%, or 1.3%, or 1.4%, or 1.5%, or 1.6%, or 1.7%, or 1.8%, or 1.9%, or 2.0%) indicates that the transplant is undergoing acute rejection.

In some embodiments, the transplant rejection is antibody mediated transplant rejection. In some embodiments, the transplant rejection is T cell mediated transplant rejection.

In some embodiments, an amount of dd-cfDNA of less than 1% (or 0.9%, or 0.8%, or 0.7%, or 0.6%, or 0.5%) indicates that the transplant is either undergoing borderline rejection, undergoing other injury, or stable.

In a further aspect, the present invention relates to a method of monitoring immunosuppressive therapy in a subject, the method comprising: extracting DNA from the blood sample of the transplant recipient, wherein the DNA comprises donor-derived cell-free DNA and recipient-derived cell-free DNA; performing universal amplification of the extracted DNA; performing targeted amplification at 500-50,000 target loci in a single reaction volume using 500-50,000 primer pairs, wherein the target loci comprise polymorphic loci and non-polymorphic loci; sequencing the amplification products by high-throughput sequencing; and quantifying the amount of donor-derived cell-free DNA in the blood sample, wherein a change in levels of dd-cfDNA over a time interval is indicative of transplant status.

In some embodiments, the method further comprising adjusting immunosuppressive therapy based on the levels of dd-cfDNA over the time interval.

In some embodiments, an increase in the levels of dd-cfDNA is indicative of transplant rejection and a need for adjusting immunosuppressive therapy. In some embodiments, no change or a decrease in the levels of dd-cfDNA indicates transplant tolerance or stability, and a need for adjusting immunosuppressive therapy.

In some embodiments, an amount of dd-cfDNA of greater than 1% (or 1.1%, or 1.2%, or 1.3%, or 1.4%, or 1.5%, or 1.6%, or 1.7%, or 1.8%, or 1.9%, or 2.0%) indicates that the transplant is undergoing acute rejection. In some embodiments, the transplant rejection is antibody mediated transplant rejection. In some embodiments, the transplant rejection is T cell mediated transplant rejection.

In some embodiments, an amount of dd-cfDNA of less than 1% (or 0.9%, or 0.8%, or 0.7%, or 0.6%, or 0.5%) indicates that the transplant is either undergoing borderline rejection, undergoing other injury, or stable.

In some embodiments, the method does not comprise genotyping the transplant donor and/or the transplant recipient.

In some embodiments, the method further comprises measuring an amount of one or more alleles at the target loci that are polymorphic loci.

In some embodiments, the target loci comprise at least 1,000 polymorphic loci, or at least 2,000 polymorphic loci, or at least 5,000 polymorphic loci, or at least 10,000 polymorphic loci.

In some embodiments, the target loci that are amplified in amplicons of about 50-100 bp in length, or about 50-90 bp in length, or about 60-80 bp in length, or about 60-75 bp in length, or about 65 bp in length.

In some embodiments, the transplant recipient is a human. In some embodiments, the transplant recipient has received a transplant selected from a kidney transplant, liver transplant, pancreas transplant, islet cell transplant, intestinal transplant, heart transplant, lung transplant, bone marrow transplant, heart valve transplant, or a skin transplant. In some embodiments, the transplant recipient has received SPK transplant.

In some embodiments, the extracting step comprises size selection to enrich for donor-derived cell-free DNA and reduce the amount of recipient-derived cell-free DNA disposed from bursting white-blood cells.

In some embodiments, the universal amplification step preferentially amplifies donor-derived cell-free DNA over recipient-derived cell-free DNA that are disposed from bursting white-blood cells.

In some embodiments, the method comprises longitudinally collecting a plurality of blood samples from the transplant recipient after transplantation, and repeating steps (a) to (e) for each blood sample collected. In some embodiments, the method comprises collecting and analyzing blood samples from the transplant recipient for a time period of about three months, or about six months, or about twelve months, or about eighteen months, or about twenty-four months, etc. In some embodiments, the method comprises collecting blood samples from the transplant recipient at an interval of about one week, or about two weeks, or about three weeks, or about one month, or about two months, or about three months, etc.

In some embodiments, the method has a sensitivity of at least 80%, or at least 85%, or at least 90%, or at least 95%, or at least 98% in identifying acute rejection (AR) over non-AR with a cutoff threshold of 1% dd-cfDNA and a confidence interval of 95%.

In some embodiments, the method has a specificity of at least 60%, or at least 65%, or at least 70%, or at least 75%, or at least 80%, or at least 85%, or at least 90% in identifying AR over non-AR with a cutoff threshold of 1% dd-cfDNA and a confidence interval of 95%.

In some embodiments, the method has an area under the curve (AUC) of at least 0.8, or 0.85, or at least 0.9, or at least 0.95 in identifying AR over non-AR with a cutoff threshold of 1% dd-cfDNA and a confidence interval of 95%.

In some embodiments, the method has a sensitivity of at least 80%, or at least 85%, or at least 90%, or at least 95%, or at least 98% in identifying AR over normal, stable allografts (STA) with a cutoff threshold of 1% dd-cfDNA and a confidence interval of 95%.

In some embodiments, the method has a specificity of at least 80%, or at least 85%, or at least 90%, or at least 95%, or at least 98% in identifying AR over STA with a cutoff threshold of 1% dd-cfDNA and a confidence interval of 95%.

In some embodiments, the method has an AUC of at least 0.8, or 0.85, or at least 0.9, or at least 0.95, or at least 0.98, or at least 0.99 in identifying AR over STA with a cutoff threshold of 1% dd-cfDNA and a confidence interval of 95%.

In some embodiments, the method has a sensitivity as determined by a limit of blank (LoB) of 0.5% or less, and a limit of detection (LoD) of 0.5% or less. In some embodiments, LoB is 0.23% or less and LoD is 0.29% or less. In some embodiments, the sensitivity is further determined by a limit of quantitation (LoQ). In some embodiments, LoQ is 10 times greater than the LoD; LoQ may be 5 times greater than the LoD; LoQ may be 1.5 times greater than the LoD; LoQ may be 1.2 times greater than the LoD; LoQ may be 1.1 times greater than the LoD; or LoQ may be equal to or greater than the LoD. In some embodiments, LoB is equal to or less than 0.04%, LoD is equal to or less than 0.05%, and/or LoQ is equal to the LoD.

In some embodiments, the method has an accuracy as determined by evaluating a linearity value obtained from linear regression analysis of measured donor fractions as a function of the corresponding attempted spike levels, wherein the linearity value is a R2 value, wherein the R2 value is from about 0.98 to about 1.0. In some embodiments, the R2 value is 0.999. In some embodiments, the method has an accuracy as determined by using linear regression on measured donor fractions as a function of the corresponding attempted spike levels to calculate a slope value and an intercept value, wherein the slope value is from about 0.9 to about 1.2 and the intercept value is from about-0.0001 to about 0.01. In some embodiments, the slope value is approximately 1, and the intercept value is approximately 0.

In some embodiments, the method has a precision as determined by calculating a coefficient of variation (CV), wherein the CV is less than about 10.0%. CV is less than about 6%. In some embodiments, the CV is less than about 4%. In some embodiments, the CV is less than about 2%. In some embodiments, the CV is less than about 1%.

In some embodiments, the AR is antibody-mediated rejection (ABMR). In some embodiments, the AR is T-cell-mediated rejection (TCMR).

Further disclosed herein are methods for detection of transplant donor-derived cell-free DNA (dd-cfDNA) in a sample from a transplant recipient. In some embodiments, in the methods disclosed herein, the transplant recipient is a mammal. In some embodiments, the transplant recipient is a human. In some embodiments, the transplant recipient has received a transplant selected from a kidney transplant, liver transplant, pancreas transplant, islet cell transplant, intestinal transplant, heart transplant, lung transplant, bone marrow transplant, heart valve transplant, or a skin transplant. In some embodiments, the transplant recipient has received SPK transplant. In some embodiments, the method may be performed on transplant recipients the day of or after transplant surgery, up to a year following transplant surgery.

In some embodiments, disclosed herein is a method of amplifying target loci of donor-derived cell-free DNA (dd-cfDNA) from a blood sample of a transplant recipient, the method comprising: a) extracting DNA from the blood sample of the transplant recipient, wherein the DNA comprises cell-free DNA derived from both the transplanted cells and from the transplant recipient, b) enriching the extracted DNA at target loci, wherein the target loci comprise 50 to 5000 target loci comprising polymorphic loci and non-polymorphic loci; and c) amplifying the target loci.

In some embodiments, disclosed herein is a method of detecting donor-derived cell-free DNA (dd-cfDNA) in a blood sample from a transplant recipient, the method comprising: a) extracting DNA from the blood sample of the transplant recipient, wherein the DNA comprises cell-free DNA derived from both the transplanted cells and from the transplant recipient, b) enriching the extracted DNA at target loci, wherein the target loci comprise 50 to 5000 target loci comprising polymorphic loci and non-polymorphic loci; c) amplifying the target loci; d) contacting the amplified target loci with probes that specifically hybridize to target loci; and e) detecting binding of the target loci with the probes, thereby detecting dd-cfDNA in the blood sample. In some embodiments, the probes are labelled with a detectable marker.

In some embodiments, disclosed herein is a method of determining the likelihood of transplant rejection within a transplant recipient, the method comprising: a) extracting DNA from the blood sample of the transplant recipient, wherein the DNA comprises cell-free DNA derived from both the transplanted cells and from the transplant recipient, b) enriching the extracted DNA at target loci, wherein the target loci comprise 50 to 5000 target loci comprising polymorphic loci and non-polymorphic loci; c) amplifying the target loci; and d) measuring an amount of transplant DNA and an amount of recipient DNA in the recipient blood sample; wherein a greater amount of dd-cfDNA indicates a greater likelihood of transplant rejection.

In some embodiments, disclosed herein is a method of diagnosing a transplant within a transplant recipient as undergoing acute rejection, the method comprising: a) extracting DNA from the blood sample of the transplant recipient, wherein the DNA comprises cell-free DNA derived from both the transplanted cells and from the transplant recipient, b) enriching the extracted DNA at target loci, wherein the target loci comprise 50 to 5000 target loci comprising polymorphic loci and non-polymorphic loci; c) amplifying the target loci; and d) measuring an amount of transplant DNA and an amount of recipient DNA in the recipient blood sample; wherein an amount of dd-cfDNA of greater than 1% (or 1.1%, or 1.2%, or 1.3%, or 1.4%, or 1.5%, or 1.6%, or 1.7%, or 1.8%, or 1.9%, or 2.0%) indicates that the transplant is undergoing acute rejection.

In some embodiments, in the methods disclosed herein, the transplant rejection is antibody mediated transplant rejection. In some embodiments, the transplant rejection is T cell mediated transplant rejection. In some embodiments, an amount of dd-cfDNA of less than 1% (or 0.9%, or 0.8%, or 0.7%, or 0.6%, or 0.5%) indicates that the transplant is either undergoing borderline rejection, undergoing other injury, or stable.

In some embodiments, disclosed herein is a method of monitoring immunosuppressive therapy in a subject, the method comprising a) extracting DNA from the blood sample of the transplant recipient, wherein the DNA comprises cell-free DNA derived from both the transplanted cells and from the transplant recipient, b) enriching the extracted DNA at target loci, wherein the target loci comprise 50 to 5000 target loci comprising polymorphic loci and non-polymorphic loci; c) amplifying the target loci; and d) measuring an amount of transplant DNA and an amount of recipient DNA in the recipient blood sample; wherein a change in levels of dd-cfDNA over a time interval is indicative of transplant status. In some embodiments, the method further comprises adjusting immunosuppressive therapy based on the levels of dd-cfDNA over the time interval. In some embodiments, an increase in the levels of dd-cfDNA are indicative of transplant rejection and a need for adjusting immunosuppressive therapy. In some embodiments, a change or a decrease in the levels of dd-cfDNA indicates transplant tolerance or stability, and a need for adjusting immunosuppressive therapy.

In some embodiments, in the methods disclosed herein, the target loci that are amplified in amplicons of about 50-100 bp in length, or about 60-80 bp in length. In some embodiments, the amplicons are about 65 bp in length.

In some embodiments, the methods disclosed herein further comprise measuring an amount of transplant DNA and an amount of recipient DNA in the recipient blood sample.

In some embodiments, the methods disclosed herein do not comprise genotyping the transplant donor and the transplant recipient.

In some embodiments, the methods disclosed herein further comprise detecting the amplified target loci using a microarray.

In some embodiments, in the methods disclosed herein, the polymorphic loci and the non-polymorphic loci are amplified in a single reaction.

In some embodiments, in the methods disclosed herein, the DNA is preferentially enriched at the target loci.

In some embodiments, preferentially enriching the DNA in the sample at the plurality of polymorphic loci includes obtaining a plurality of pre-circularized probes where each probe targets one of the polymorphic loci, and where the 3' and 5' end of the probes are designed to hybridize to a region of DNA that is separated from the polymorphic site of the locus by a small number of bases, where the small number is 1, 2, 3, 4, 5, 6, 7, 8, 9, 10, 11, 12, 13, 14, 15, 16, 17, 18, 19, 20, 21 to 25, 26 to 30, 31 to 60, or a combination thereof, hybridizing the pre-circularized probes to DNA from the sample, filling the gap between the hybridized probe ends using DNA polymerase, circularizing the pre-circularized probe, and amplifying the circularized probe.

In some embodiments, preferentially enriching the DNA at the plurality of polymorphic loci includes obtaining a plurality of ligation-mediated PCR probes where each PCR probe targets one of the polymorphic loci, and where the upstream and downstream PCR probes are designed to hybridize to a region of DNA, on one strand of DNA, that is separated from the polymorphic site of the locus by a small number of bases, where the small number is 1, 2, 3, 4, 5, 6, 7, 8, 9, 10, 11, 12, 13, 14, 15, 16, 17, 18, 19, 20, 21 to 25, 26 to 30, 31 to 60, or a combination thereof, hybridizing the ligation-mediated PCR probes to the DNA from the first sample, filling the gap between the ligation-mediated PCR probe ends using DNA polymerase, ligating the ligation-mediated PCR probes, and amplifying the ligated ligation-mediated PCR probes.

In some embodiments, preferentially enriching the DNA at the plurality of polymorphic loci includes obtaining a plurality of hybrid capture probes that target the polymorphic loci, hybridizing the hybrid capture probes to the DNA in the sample and physically removing some or all of the unhybridized DNA from the first sample of DNA.

In some embodiments, the hybrid capture probes are designed to hybridize to a region that is flanking but not overlapping the polymorphic site. In some embodiments, the hybrid capture probes are designed to hybridize to a region that is flanking but not overlapping the polymorphic site, and where the length of the flanking capture probe may be selected from the group consisting of less than about 120 bases, less than about 110 bases, less than about 100 bases, less than about 90 bases, less than about 80 bases, less than about 70 bases, less than about 60 bases, less than about 50 bases, less than about 40 bases, less than about 30 bases, and less than about 25 bases. In some embodiments, the hybrid capture probes are designed to hybridize to a region that overlaps the polymorphic site, and where the plurality of hybrid capture probes comprise at least two hybrid capture probes for each polymorphic loci, and where each hybrid capture probe is designed to be complementary to a different allele at that polymorphic locus.

In some embodiments, preferentially enriching the DNA at a plurality of polymorphic loci includes obtaining a plurality of inner forward primers where each primer targets one of the polymorphic loci, and where the 3' end of the inner forward primers are designed to hybridize to a region of DNA upstream from the polymorphic site, and separated from the polymorphic site by a small number of bases, where the small number is selected from the group consisting of 1, 2, 3, 4, 5, 6 to 10, 11 to 15, 16 to 20, 21 to 25, 26 to 30, or 31 to 60 base pairs, optionally obtaining a plurality of inner reverse primers where each primer targets one of the polymorphic loci, and where the 3' end of the inner reverse primers are designed to hybridize to a region of DNA upstream from the polymorphic site, and separated from the polymorphic site by a small number of bases, where the small number is selected from the group consisting of 1, 2, 3, 4, 5, 6 to 10, 11 to 15, 16 to 20, 21 to 25, 26 to 30, or 31 to 60 base pairs, hybridizing the inner primers to the DNA, and amplifying the DNA using the polymerase chain reaction to form amplicons.

In some embodiments, the method also includes obtaining a plurality of outer forward primers where each primer targets one of the polymorphic loci, and where the outer forward primers are designed to hybridize to the region of DNA upstream from the inner forward primer, optionally obtaining a plurality of outer reverse primers where each primer targets one of the polymorphic loci, and where the outer reverse primers are designed to hybridize to the region of DNA immediately downstream from the inner reverse primer, hybridizing the first primers to the DNA, and amplifying the DNA using the polymerase chain reaction.

In some embodiments, the method also includes obtaining a plurality of outer reverse primers where each primer targets one of the polymorphic loci, and where the outer reverse primers are designed to hybridize to the region of DNA immediately downstream from the inner reverse primer, optionally obtaining a plurality of outer forward primers where each primer targets one of the polymorphic loci, and where the outer forward primers are designed to hybridize to the region of DNA upstream from the inner forward primer, hybridizing the first primers to the DNA, and amplifying the DNA using the polymerase chain reaction.

In some embodiments, preparing the first sample further includes appending universal adapters to the DNA in the first sample and amplifying the DNA in the first sample using the polymerase chain reaction. In some embodiments, at least a fraction of the amplicons that are amplified are less than 100 bp, less than 90 bp, less than 80 bp, less than 70 bp, less than 65 bp, less than 60 bp, less than 55 bp, less than 50 bp, or less than 45 bp, and where the fraction is 10%, 20%, 30%, 40%, 50%, 60%, 70%, 80%, 90%, or 99%.

In some embodiments, amplifying the DNA is done in one or a plurality of individual reaction volumes, and where each individual reaction volume contains more than 100 different forward and reverse primer pairs, more than 200 different forward and reverse primer pairs, more than 500 different forward and reverse primer pairs, more than 1,000 different forward and reverse primer pairs, more than 2,000 different forward and reverse primer pairs, more than 5,000 different forward and reverse primer pairs, more than 10,000 different forward and reverse primer pairs, more than 20,000 different forward and reverse primer pairs, more than 50,000 different forward and reverse primer pairs, or more than 100,000 different forward and reverse primer pairs.

In some embodiments, preparing the sample further comprises dividing the sample into a plurality of portions, and where the DNA in each portion is preferentially enriched at a subset of the plurality of polymorphic loci. In some embodiments, the inner primers are selected by identifying primer pairs likely to form undesired primer duplexes and removing from the plurality of primers at least one of the pair of primers identified as being likely to form undesired primer duplexes. In some embodiments, the inner primers contain a region that is designed to hybridize either upstream or downstream of the targeted polymorphic locus, and optionally contain a universal priming sequence designed to allow PCR amplification. In some embodiments, at least some of the primers additionally contain a random region that differs for each individual primer molecule. In some embodiments, at least some of the primers additionally contain a molecular barcode.

In some embodiments, the method comprises: (a) performing multiplex polymerase chain reaction (PCR) on a nucleic acid sample comprising target loci to simultaneously amplify at least 1,000 distinct target loci using either (i) at least 1,000 different primer pairs, or (ii) at least 1,000 target-specific primers and a universal or tag-specific primer, in a single reaction volume to produce amplified products comprising target amplicons; and (b) sequencing the amplified products. In some embodiments, the method does not comprise using a microarray.

In some embodiments, the method comprises (a) performing multiplex polymerase chain reaction (PCR) on the cell free DNA sample comprising target loci to simultaneously amplify at least 1,000 distinct target loci using either (i) at least 1,000 different primer pairs, or (ii) at least 1,000 target-specific primers and a universal or tag-specific primer, in a single reaction volume to produce amplified products comprising target amplicons; and b) sequencing the amplified products. In some embodiments, the method does not comprise using a microarray.

In some embodiments, the method also includes obtaining genotypic data from one or both of the transplant donor and the transplant recipient. In some embodiments, obtaining genotypic data from one or both of the transplant donor and the transplant recipient includes preparing the DNA from the donor and the recipient where the preparing comprises preferentially enriching the DNA at the plurality of polymorphic loci to give prepared DNA, optionally amplifying the prepared DNA, and measuring the DNA in the prepared sample at the plurality of polymorphic loci.

In some embodiments, building a joint distribution model for the expected allele count probabilities of the plurality of polymorphic loci on the chromosome is done using the obtained genetic data from the one or both of the transplant donor and the transplant recipient. In some embodiments, the first sample has been isolated from transplant recipient plasma and where the obtaining genotypic data from the transplant recipient is done by estimating the recipient genotypic data from the DNA measurements made on the prepared sample.

In some embodiments, preferential enrichment results in average degree of allelic bias between the prepared sample and the first sample of a factor selected from the group consisting of no more than a factor of 2, no more than a factor of 1.5, no more than a factor of 1.2, no more than a factor of 1.1, no more than a factor of 1.05, no more than a factor of 1.02, no more than a factor of 1.01, no more than a factor of 1.005, no more than a factor of 1.002, no more than a factor of 1.001 and no more than a factor of 1.0001. In some embodiments, the plurality of polymorphic loci are SNPs. In some embodiments, measuring the DNA in the prepared sample is done by sequencing.

In some embodiments, a diagnostic box is disclosed for helping to determine transplant status in a transplant recipient where the diagnostic box is capable of executing the preparing and measuring steps of the disclosed methods.

In some embodiments, the allele counts are probabilistic rather than binary. In some embodiments, measurements of the DNA in the prepared sample at the plurality of polymorphic loci are also used to determine whether or not the transplant has inherited one or a plurality of linked haplotypes.

In some embodiments, building a joint distribution model for allele count probabilities is done by using data about the probability of chromosomes crossing over at different locations in a chromosome to model dependence between polymorphic alleles on the chromosome. In some embodiments, building a joint distribution model for allele counts and the step of determining the relative probability of each hypothesis are done using a method that does not require the use of a reference chromosome.

In some embodiments, determining the relative probability of each hypothesis makes use of an estimated fraction of donor-derived cell-free DNA (dd-cfDNA) in the prepared sample. In some embodiments, the DNA measurements from the prepared sample used in calculating allele count probabilities and determining the relative probability of each hypothesis comprise primary genetic data. In some embodiments, selecting the transplant status corresponding to the hypothesis with the greatest probability is carried out using maximum likelihood estimates or maximum a posteriori estimates.

In some embodiments, calling the transplant status also includes combining the relative probabilities of each of the status hypotheses determined using the joint distribution model and the allele count probabilities with relative probabilities of each of the status hypotheses that are calculated using statistical techniques taken from a group consisting of a read count analysis, comparing heterozygosity rates, a statistic that is only available when donor genetic information is used, the probability of normalized genotype signals for certain donor/recipient contexts, a statistic that is calculated using an estimated transplant fraction of the first sample or the prepared sample, and combinations thereof.

In some embodiments, a confidence estimate is calculated for the called transplant status. In some embodiments, the method also includes taking a clinical action based on the called transplant status.

In some embodiments, a report displaying a determined transplant status is generated using the method. In some embodiments, a kit is disclosed for determining a transplant status designed to be used with the methods disclosed herein, the kit including a plurality of inner forward primers and optionally the plurality of inner reverse primers, where each of the primers is designed to hybridize to the region of DNA immediately upstream and/or downstream from one of the polymorphic sites on the target chromosome, and optionally additional chromosomes, where the region of hybridization is separated from the polymorphic site by a small number of bases, where the small number is selected from the group consisting of 1, 2, 3, 4, 5, 6 to 10, 11 to 15, 16 to 20, 21 to 25, 26 to 30, 31 to 60, and combinations thereof.

In some embodiments, the methods disclosed herein comprise a selection step to select for shorter cfDNA.

In some embodiments, the methods disclosed herein comprise a universal application step to enrich for cfDNA.

In some embodiments, the determination that the amount of dd-cfDNA above a cutoff threshold is indicative of acute rejection of the transplant. Machine learning may be used to resolve rejection vs non-rejection.

In some embodiments, the cutoff threshold value is expressed as percentage of dd-cfDNA (dd-cfDNA %) in the blood sample.

In some embodiments, the cutoff threshold value is expressed as copy number of dd-cfDNA per volume unit of the blood sample.

In some embodiments, the cutoff threshold value is expressed as copy number of dd-cfDNA per volume unit of the blood sample multiplied by body mass or blood volume of the transplant recipient.

In some embodiments, the cutoff threshold value takes into account the body mass or blood volume of the patient.

In some embodiments, the cutoff threshold value takes into account one or more of the followings: donor genome copies per volume of plasma, cell-free DNA yield per volume of plasma, donor height, donor weight, donor age, donor gender, donor ethnicity, donor organ mass, donor organ, live vs deceased donor, related vs unrelated donor, recipient height, recipient weight, recipient age, recipient gender, recipient ethnicity, creatinine, eGFR (estimated glomerular filtration rate), cfDNA methylation, DSA (donor-specific antibodies), KDPI (kidney donor profile index), medications (immunosuppression, steroids, blood thinners, etc.), infections (BKV, EBV, CMV, UTI), recipient and/or donor HLA alleles or epitope mismatches, Banff classification of renal allograft pathology, and for-cause vs surveillance or protocol biopsy.

In some embodiments, the cutoff threshold value is scaled according to the amount of total cfDNA in the blood sample.

In some embodiments, the method has a sensitivity of at least 80% in identifying acute rejection (AR) over non-AR when the dd-cfDNA amount is above the cutoff threshold value scaled according to the amount of total cfDNA in the blood sample and a confidence interval of 95%.

In some embodiments, the method has a specificity of at least 70% in identifying acute rejection (AR) over non-AR when the dd-cfDNA amount is above the cutoff threshold value scaled according to the amount of total cfDNA in the blood sample and a confidence interval of 95%.

In some embodiments, the method has a sensitivity of at least 80% in identifying acute rejection (AR) over non-AR when the dd-cfDNA amount is above the cutoff threshold value scaled according to the amount of total cfDNA in the blood sample and a confidence interval of 95%. In some embodiments, the method has a sensitivity of at least 85% in identifying acute rejection (AR) over non-AR when the dd-cfDNA amount is above the cutoff threshold value scaled according to the amount of total cfDNA in the blood sample and a confidence interval of 95%. In some embodiments, the method has a sensitivity of at least 90% in identifying acute rejection (AR) over non-AR when the dd-cfDNA amount is above the cutoff threshold value scaled according to the amount of total cfDNA in the blood sample and a confidence interval of 95%. In some embodiments, the method has a sensitivity of at least 95% in identifying acute rejection (AR) over non-AR when the dd-cfDNA amount is be above the cutoff threshold value scaled according to the amount of total cfDNA in the blood sample and a confidence interval of 95%.

In some embodiments, the method has a specificity of at least 70% in identifying acute rejection (AR) over non-AR when the dd-cfDNA amount is above the cutoff threshold value scaled according to the amount of total cfDNA in the blood sample and a confidence interval of 95%. In some embodiments, the method has a specificity of at least 75% in identifying acute rejection (AR) over non-AR when the dd-cfDNA amount is above the cutoff threshold value scaled according to the amount of total cfDNA in the blood sample and a confidence interval of 95%. In some embodiments, the method has a specificity of at least 85% in identifying acute rejection (AR) over non-AR when the dd-cfDNA amount is above the cutoff threshold value scaled according to the amount of total cfDNA in the blood sample and a confidence interval of 95%. In some embodiments, the method has a specificity of at least 90% in identifying acute rejection (AR) over non-AR when the dd-cfDNA amount is above the cutoff threshold value scaled according to the amount of total cfDNA in the blood sample and a confidence interval of 95%. In some embodiments, the method has a specificity of at least 95% in identifying acute rejection (AR) over non-AR when the dd-cfDNA amount is above the cutoff threshold value scaled according to the amount of total cfDNA in the blood sample and a confidence interval of 95%.

Multiplex Amplification

In some embodiments, the method comprises performing a multiplex amplification reaction to amplify a plurality of polymorphic loci in one reaction mixture before determining the sequences of the selectively enriched DNA.

In certain illustrative embodiments, the nucleic acid sequence data is generated by performing high throughput DNA sequencing of a plurality of copies of a series of amplicons generated using a multiplex amplification reaction, wherein each amplicon of the series of amplicons spans at least one polymorphic locus of the set of polymorphic loci and wherein each of the polymeric loci of the set is amplified. For example, in these embodiments a multiplex PCR to amplify amplicons across at least 100; 200; 500; 1,000; 2,000; 5,000; 10,000; 20,000; 50,000; or 100,000 polymorphic loci (e.g., SNP loci) may be performed. This multiplex reaction can be set up as a single reaction or as pools of different subset multiplex reactions. The multiplex reaction methods provided herein, such as the massive multiplex PCR disclosed herein provide an exemplary process for carrying out the amplification reaction to help attain improved multiplexing and therefore, sensitivity levels.

In some embodiments, amplification is performed using direct multiplexed PCR, sequential PCR, nested PCR, doubly nested PCR, one-and-a-half sided nested PCR, fully nested PCR, one sided fully nested PCR, one-sided nested PCR, hemi-nested PCR, hemi-nested PCR, triply hemi-nested PCR, semi-nested PCR, one sided semi-nested PCR, reverse semi-nested PCR method, or one-sided PCR, which are described in U.S. application Ser. No. 13/683,604, filed Nov. 21, 2012, U.S. Publication No. 2013/0123120, U.S. application Ser. No. 13/300,235, filed Nov. 18, 2011, U.S. Publication No 2012/0270212, and U.S. Ser. No. 61/994,791, filed May 16, 2014, all of which are hereby incorporated by reference in their entirety.

In some embodiments, multiplex PCR is used. In some embodiments, the method of amplifying target loci in a nucleic acid sample involves (i) contacting the nucleic acid sample with a library of primers that simultaneously hybridize to at least 100; 200; 500; 1,000; 2,000; 5,000; 10,000; 20,000; 50,000; or 100,000 different target loci to produce a single reaction mixture; and (ii) subjecting the reaction mixture to primer extension reaction conditions (such as PCR conditions) to produce amplified products that include target amplicons. In some embodiments, at least 50, 60, 70, 80, 90, 95, 96, 97, 98, 99, or 99.5% of the targeted loci are amplified. In various embodiments, less than 60, 50, 40, 30, 20, 10, 5, 4, 3, 2, 1, 0.5, 0.25, 0.1, or 0.05% of the amplified products are primer dimers. In some embodiments, the primers are in solution (such as being dissolved in the liquid phase rather than in a solid phase). In some embodiments, the primers are in solution and are not immobilized on a solid support. In some embodiments, the primers are not part of a microarray.

In certain embodiments, the multiplex amplification reaction is performed under limiting primer conditions for at least ½ of the reactions. In some embodiments, limiting primer concentrations are used in 1/10, 1/5, ¼, 1/3, ½, or all of the reactions of the multiplex reaction. Provided herein are factors to consider in achieving limiting primer conditions in an amplification reaction such as PCR.

In certain embodiments, the multiplex amplification reaction can include, for example, between 2,500 and 50,000 multiplex reactions. In certain embodiments, the following ranges of multiplex reactions are performed: between 100, 200, 250, 500, 1000, 2500, 5000, 10,000, 20,000, 25000, 50000 on the low end of the range and between 200, 250, 500, 1000, 2500, 5000, 10,000, 20,000, 25000, 50000, and 100,000 on the high end of the range.

In an embodiment, a multiplex PCR assay is designed to amplify potentially heterozygous SNP or other polymorphic or non-polymorphic loci on one or more chromosomes and these assays are used in a single reaction to amplify DNA. The number of PCR assays may be between 50 and 200 PCR assays, between 200 and 1,000 PCR assays, between 1,000 and 5,000 PCR assays, or between 5,000 and 20,000 PCR assays (50 to 200-plex, 200 to 1,000-plex, 1,000 to 5,000-plex, 5,000 to 20,000-plex, more than 20,000-plex respectively). In an embodiment, a multiplex pool of at least 10,000 PCR assays (10,000-plex) are designed to amplify potentially heterozygous SNP loci a single reaction to amplify cfDNA obtained from a blood, plasma, serum, solid tissue, or urine sample. The SNP frequencies of each locus may be determined by clonal or some other method of sequencing of the amplicons. In another embodiment the original cfDNA samples is split into two samples and parallel 5,000-plex assays are performed. In another embodiment the original cfDNA samples is split into n samples and parallel (~10,000/n)-plex assays are performed where n is between 2 and 12, or between 12 and 24, or between 24 and 48, or between 48 and 96.

In an embodiment, a method disclosed herein uses highly efficient highly multiplexed targeted PCR to amplify DNA followed by high throughput sequencing to determine the allele frequencies at each target locus. One technique that allows highly multiplexed targeted PCR to perform in a highly efficient manner involves designing primers that are unlikely to hybridize with one another. The PCR probes, typically referred to as primers, are selected by creating a thermodynamic model of potentially adverse interactions between at least 100, at least 200, at least 500, at least 1,000, at least 2,000, at least 5,000, at least 10,000, at least 20,000, or at least 50,000 potential primer pairs, or unintended interactions between primers and sample DNA, and then using the model to eliminate designs that are incompatible with other the designs in the pool. Another technique that allows highly multiplexed targeted PCR to perform in a highly efficient manner is using a partial or full nesting approach to the targeted PCR. Using one or a combination of these approaches allows multiplexing of at least 100, at least 200, at least 500, at least 1,000, at least 2,000, at least 5,000, at least 10,000, at least 20,000, or at least 50,000 primers in a single pool with the resulting amplified DNA comprising a majority of DNA molecules that, when sequenced, will map to targeted loci. Using one or a combination of these approaches allows multiplexing of a large number of primers in a single pool with the resulting amplified DNA comprising greater than 50%, greater than 80%, greater than 90%, greater than 95%, greater than 98%, or greater than 99% DNA molecules that map to targeted loci.

Bioinformatics methods are used to analyze the genetic data obtained from multiplex PCR. The bioinformatics methods useful and relevant to the methods disclosed herein can be found in U.S. Patent Publication No. 2018/0025109, incorporated by reference herein.

High-Throughput Sequencing

In some embodiments, the sequences of the amplicons are determined by performing high-throughput sequencing.

The genetic data of the transplant recipient and/or of the transplant donor can be transformed from a molecular state to an electronic state by measuring the appropriate genetic material using tools and or techniques taken from a group including, but not limited to: genotyping microarrays, and high throughput sequencing. Some high throughput sequencing methods include Sanger DNA sequencing, pyrosequencing, the ILLUMINA SOLEXA platform, ILLUMINA's GENOME ANALYZER, or APPLIED BIOSYSTEM's 454 sequencing platform, HELICOS's TRUE SINGLE MOLECULE SEQUENCING platform, HALCYON MOLECULAR's electron microscope sequencing method, or any other sequencing method. In some embodiments, the high throughput sequencing is performed on Illumina NextSeq®, followed by demultiplexing and mapping to the human reference genome. All of these methods physically transform the genetic data stored in a sample of DNA into a set of genetic data that is typically stored in a memory device en route to being processed.

In some embodiments, the sequences of the selectively enriched DNA are determined by performing microarray analysis. In an embodiment, the microarray may be an ILLUMINA SNP microarray, or an AFFYMETRIX SNP microarray.

In some embodiments, the sequences of the selectively enriched DNA are determined by performing quantitative PCR (qPCR) or digital droplet PCR (ddPCR) analysis. qPCR measures the intensity of fluorescence at specific times (generally after every amplification cycle) to determine the relative amount of target molecule (DNA). ddPCR measures the actual number of molecules (target DNA) as each molecule is in one droplet, thus making it a discrete "digital" measurement. It provides absolute quantification because ddPCR measures the positive fraction of samples, which is the number of droplets that are fluorescing due to proper amplification. This positive fraction accurately indicates the initial amount of template nucleic acid.

Tracer DNA and Use Thereof

Tracer DNA for estimating the amount of total cfDNA in a sample is described in U.S. Prov. Appl. No. 63/031,879 filed May 29, 2020 and titled "Improved Methods for Detection of Donor Derived Cell-Free DNA", which is incorporated herein by reference in its entirety. In some embodiments, the Tracer DNA comprises synthetic double-stranded DNA molecules. In some embodiments, the Tracer DNA comprises DNA molecules of non-human origin.

In some embodiments, the Tracer DNA comprises DNA molecules having a length of about 50-500 bp, or about 75-300 bp, or about 100-250 bp, or about 125-200 bp, or about 125 bp, or about 160 bp, or about 200 bp, or about 500-1,000 bp.

In some embodiments, the Tracer DNA comprises DNA molecules having the same or substantially the same length, such as a DNA molecule having a length of about 125 bp, or about 160 bp, or about 200 bp. In some embodiments, the Tracer DNA comprises DNA molecules having different lengths, such as a first DNA molecule having a length of about 125 bp, a second DNA molecule having a length of about 160 bp, and a third DNA molecule having a length of about 200 bp. In some embodiments, the DNA molecules having different lengths are used to determine size distribution of the cell-free DNA in the sample In some embodiments, the Tracer DNA comprises a target sequence, wherein the target sequence comprises a barcode positioned between a pair of primer binding sites capable of binding to a pair of primers. In some embodiments, at least part of the Tracer DNA is designed based on an endogenous human SNP locus, by replacing an endogenous sequence containing the SNP locus with the barcode. During the mmPCR target enrichment step, the primer pair targeting the SNP locus can also amplify the portion of Tracer DNA containing the barcode.

In some embodiments, the barcode is an arbitrary barcode. In some embodiments, the barcode comprises reverse complement of a corresponding endogenous genome sequence capable of being amplified by the same primer pair.

In some embodiments, the target sequence within the Tracer DNA is flanked on one or both sides by endogenous genome sequences. In some embodiments, the target sequence within the Tracer DNA is flanked on one or both sides by non-endogenous sequences.

In some embodiments, the Tracer DNA comprises a plurality of target sequences. In some embodiments, the Tracer DNA comprises a first target sequence comprising a first barcode positioned between a first pair of primer binding sites capable of binding to a first pair of primers, and a second barcode positioned between a second pair of primer binding sites capable of binding to a second pair of primers. In some embodiments, the first and/or second target sequence is designed based on one or more endogenous human SNP loci, by replacing an endogenous sequence containing a SNP locus with a barcode. In some embodiments, the first and/or second barcode is an arbitrary barcode. In some embodiments, the first and/or second barcode comprises reverse complement of a corresponding endogenous genome sequence capable of being amplified by the first or second primer pair. In some embodiments, the first and/or second target sequence within the Tracer DNA is flanked on one or both sides by endogenous genome sequences. In some embodiments, the first and/or second target sequence within the Tracer DNA is flanked on one or both sides by non-endogenous sequences.

In some embodiments, the Tracer DNA comprises DNA molecules having the same or substantially the same sequence. In some embodiments, the Tracer DNA comprises DNA molecules having different sequences.

In some embodiments, the Tracer DNA comprises a first DNA comprising a first target sequence and a second DNA comprising a second target sequence. In some embodiments, the first target sequence and second target sequence have different barcodes positioned between the same primer binding sites. In some embodiments, the first target sequence and second target sequence have different barcodes positioned between the same primer binding sites, wherein the different barcodes have the same or substantially the same lengths. In some embodiments, the first target sequence and second target sequence have different barcodes positioned between the same primer binding sites, wherein the different barcodes have different lengths. In some embodiments, the first target sequence and second target sequence are designed based on different endogenous human SNP loci, and hence comprise different primer binding sites. In some embodiments, the amount of first DNA and the amount of the second DNA are the same or substantially the same in the Tracer DNA. In some embodiments, the amount of first DNA and the amount of the second DNA are different in the Tracer DNA.

Determining Amount of Total Cell-Free DNA Using Tracer DNA

In certain embodiments, Tracer DNA can be used to improve accuracy and precision of the method described herein, help quantify over a wider input range, assess efficiency of different steps at different size ranges, and/or calculate fragment size-distribution of input material.

Some embodiments of the present invention relate to a method of quantifying the amount of total cell-free DNA in a biological sample, comprising: a) isolating cell-free DNA from the biological sample, wherein a first Tracer DNA is added before or after isolation of the cell-free DNA; b) performing targeted amplification at 100 or more different target loci in a single reaction volume using 100 or more different primer pairs; c) sequencing the amplification products by high-throughput sequencing to generate sequencing reads; and d) quantifying the amount of total cell-free DNA using sequencing reads derived from the first Tracer DNA.

In some embodiments, the method comprises adding the first Tracer DNA to a whole blood sample before plasma extraction. In some embodiments, the method comprises adding the first Tracer DNA to a plasma sample after plasma extraction and before isolation of the cell-free DNA. In some embodiments, the method comprises adding the first Tracer DNA to a composition comprising the isolated cell-free DNA. In some embodiments, the method comprises ligating adaptors to the isolated cell-free DNA to obtain a composition comprising adaptor-ligated DNA, and adding the first Tracer DNA to the composition comprising adaptor-ligated DNA.

In some embodiments, the method further comprises adding a second Tracer DNA before the targeted amplification. In some embodiments, the method further comprises adding a second Tracer DNA after the targeted amplification.

In some embodiments, the amount of total cfDNA in the sample is estimated using the NOR of the Tracer DNA (identifiable by the barcode), the NOR of sample DNA, and the known amount of the Tracer DNA added to the plasma sample. In some embodiments, the ratio between the NOR of the Tracer DNA and the NOR of sample DNA is used to quantify the amount of total cell-free DNA. In some embodiments, the ratio between the NOR of the barcode and the NOR of the corresponding endogenous genome sequence is used to quantify the amount of total cell-free DNA. In some embodiments, this information along with the plasma volume can also be used to calculate the amount of cfDNA per volume of plasma. In some embodiments, these can be multiplied by the percentage of donor DNA to calculate the total donor cfDNA and the donor cfDNA per volume of plasma.

Accordingly, in another aspect, the present invention relates to a method of quantifying the amount of total cell-free DNA in a biological sample, comprising: a) isolating cell-free DNA from the biological sample, wherein a first Tracer DNA composition is added before or after isolation of the cell-free DNA; b) performing targeted amplification at 100 or more different target loci in a single reaction volume using 100 or more different primer pairs; c) sequencing the amplification products by high-throughput sequencing to generate sequencing reads; and d) quantifying the amount of total cell-free DNA using sequencing reads derived from the first Tracer DNA composition.

In further aspect, the present invention relates to a method of quantifying the amount of donor-derived cell-free DNA in a biological sample of a transplant recipient, comprising: a) isolating cell-free DNA from the biological sample of the transplant recipient, wherein the isolated cell-free DNA comprises donor-derived cell-free DNA and recipient-derived cell-free DNA, wherein a first Tracer DNA composition is added before or after isolation of the cell-free DNA; b) performing targeted amplification at 100 or more different target loci in a single reaction volume using 100 or more different primer pairs; c) sequencing the amplification products by high-throughput sequencing to generate sequencing reads; and d) quantifying the amount of donor-derived cell-free DNA and the amount of total cell-free DNA, wherein the amount of total cell-free DNA is quantified using sequencing reads derived from the first Tracer DNA composition.

In a further aspect, the present invention relates to a method of determining the occurrence or likely occurrence of transplant rejection, comprising: a) isolating cell-free DNA from a biological sample of a transplant recipient, wherein the isolated cell-free DNA comprises donor-derived cell-free DNA and recipient-derived cell-free DNA, wherein a first Tracer DNA composition is added before or after isolation of the cell-free DNA; b) performing targeted amplification at 100 or more different target loci in a single reaction volume using 100 or more different primer pairs; c) sequencing the amplification products by high-throughput sequencing to generate sequencing reads; d) quantifying the amount of donor-derived cell-free DNA and the amount of total cell-free DNA, wherein the amount of total cell-free DNA is quantified using sequencing reads derived from the first Tracer DNA composition, and determining the occurrence or likely occurrence of transplant rejection using the amount of donor-derived cell-free DNA by comparing the amount of donor-derived cell-free DNA to a threshold value, wherein the threshold value is determined according to the amount of total cell-free DNA.

In some embodiments, the threshold value is a function of the number of sequencing reads of the donor-derived cell-free DNA.

In some embodiments, the method further comprises flagging the sample if the amount of total cell-free DNA falls outside a pre-determined range. In some embodiments, the method further comprises flagging the sample if the amount of total cell-free DNA is above a pre-determined value. In some embodiments, the method further comprises flagging the sample if the amount of total cell-free DNA is below a pre-determined value.

In some embodiments, the method comprises adding the first Tracer DNA composition to a whole blood sample before plasma extraction. In some embodiments, the method comprises adding the first Tracer DNA composition to a plasma sample after plasma extraction and before isolation of the cell-free DNA. In some embodiments, the method comprises adding the first Tracer DNA composition to a composition comprising the isolated cell-free DNA. In some embodiments, the method comprises ligating adaptors to the isolated cell-free DNA to obtain a composition comprising adaptor-ligated DNA, and adding the first Tracer DNA composition to the composition comprising adaptor-ligated DNA.

In some embodiments, the method further comprises adding a second Tracer DNA composition before the targeted amplification. In some embodiments, the method further comprises adding a second Tracer DNA composition after the targeted amplification.

In some embodiments, the first and/or second Tracer DNA composition comprises a plurality of DNA molecules having different sequences.

In some embodiments, the first and/or second Tracer DNA composition comprises a plurality of DNA molecules having at different concentrations.

In some embodiments, the first and/or second Tracer DNA composition comprises a plurality of DNA molecules having different lengths. In some embodiments, the plurality of DNA molecules having different lengths are used to determine size distribution of the cell-free DNA in the sample.

In some embodiments, the first and/or second Tracer DNA composition comprises a plurality of DNA molecules of non-human origin.

In some embodiments, the first and/or second Tracer DNA composition each comprises a target sequence, wherein the target sequence comprises a barcode positioned between a pair of primer binding sites capable of binding to one of the primer pairs. In some embodiments, the barcode comprises reverse complement of a corresponding endogenous genome sequence capable of being amplified by the same primer pair.

In some embodiments, the ratio between the number of reads of the Tracer DNA and the number of reads of sample DNA is used to quantify the amount of total cell-free DNA. In some embodiments, the ratio between the number of reads of the barcode and the number of reads of the corresponding endogenous genome sequence is used to quantify the amount of total cell-free DNA.

In some embodiments, the target sequence is flanked on one or both sides by endogenous genome sequences. In some embodiments, the target sequence is flanked on one or both sides by non-endogenous sequences.

In some embodiments, the first and/or second Tracer DNA composition comprises synthetic double-stranded DNA molecules. In some embodiments, the first and/or second Tracer DNA composition comprises DNA molecules having a length of 50-500 bp. In some embodiments, the first and/or second Tracer DNA composition comprises DNA molecules having a length of 75-300 bp. In some embodiments, the first and/or second Tracer DNA composition comprises DNA molecules having a length of 100-250 bp. In some embodiments, the first and/or second Tracer DNA composition comprises DNA molecules having a length of 125-200 bp. In some embodiments, the first and/or second Tracer DNA composition comprises DNA molecules having a length of about 200 bp. In some embodiments, the first and/or second Tracer DNA composition comprises DNA molecules having a length of about 160 bp. In some embodiments, the first and/or second Tracer DNA composition comprises DNA molecules having a length of about 125 bp. In some embodiments, the first and/or second Tracer DNA composition comprises DNA molecules having a length of 500-1,000 bp.

In some embodiments, the targeted amplification comprises amplifying at least 100 polymorphic or SNP loci in a single reaction volume. In some embodiments, the targeted amplification comprises amplifying at least 200 polymorphic or SNP loci in a single reaction volume. In some embodiments, the targeted amplification comprises amplifying at least 500 polymorphic or SNP loci in a single reaction volume. In some embodiments, the targeted amplification comprises amplifying at least 1,000 polymorphic or SNP loci in a single reaction volume. In some embodiments, the targeted amplification comprises amplifying at least 2,000 polymorphic or SNP loci in a single reaction volume. In some embodiments, the targeted amplification comprises amplifying at least 5,000 polymorphic or SNP loci in a single reaction volume. In some embodiments, the targeted amplification comprises amplifying at least 10,000 polymorphic or SNP loci in a single reaction volume.

In some embodiments, each primer pair is designed to amplify a target sequence of about 35 to 200 bp. In some embodiments, each primer pair is designed to amplify a target sequence of about 50 to 100 bp. In some embodiments, each primer pair is designed to amplify a target sequence of about 60 to 75 bp. In some embodiments, each primer pair is designed to amplify a target sequence of about 65 bp.

In some embodiments, the transplant recipient is a human subject. In some embodiments, the transplant recipient received an allograft. In some embodiments, the transplant recipient received a xenograft.

In some embodiments, the transplant is a human transplant. In some embodiments, the transplant is a pig transplant. In some embodiments, the transplant is from a non-human animal.

In some embodiments, the transplant is an organ transplant, tissue transplant, or cell transplant. In some embodiments, the transplant is a kidney transplant, liver transplant, pancreas transplant, intestinal transplant, heart transplant, lung transplant, heart/lung transplant, stomach transplant, testis transplant, penis transplant, ovary transplant, uterus transplant, thymus transplant, face transplant, hand transplant, leg transplant, bone transplant, bone marrow transplant, cornea transplant, skin transplant, pancreas islet cell transplant, heart valve transplant, blood vessel transplant, or blood transfusion.

In some embodiments, the method further comprises determine the transplant rejection as antibody mediated transplant rejection, T-cell mediated transplant rejection, graft injury, viral infection, bacterial infection, or borderline rejection. In some embodiments, the method further comprises determining the likelihood of one or more cancers. Cancer screening, detection, and monitoring are disclosed in PCT Patent Publication Nos. WO2015/164432, WO2017/181202, WO2018/083467, and WO2019/200228, each of which is incorporated herein by reference in its entirety. In other embodiments, the invention relates to screening a patient to determine their predicted responsiveness, or resistance, to one or more cancer treatments. This determination can be made by determining the existence of wild-type vs. mutated forms of a target gene, or in some cases the increased or over-expression of a target gene. Examples of such target screens include KRAS, NRAS, EGFR, ALK, KIT, and others. For example, a variety of KRAS mutations are appropriate for screening in accordance with the invention including, but not limited to, G12C, G12D, G12V, G13C, G13D, A18D, Q61H, K117N. In addition, PCT Patent Publication Nos. WO2015/164432, WO2017/181202, WO2018/083467, and WO2019/200228, which are incorporated herein by reference in their entirety.

In some embodiments, the method is performed without prior knowledge of donor genotypes. In some embodiments, the method is performed without prior knowledge of recipient genotypes. In some embodiments, the method is performed without prior knowledge of donor and/or recipient genotypes. In some embodiments, no genotyping of either the donor or the recipient is required prior to performing the method.

In some embodiments, the biological sample is a blood sample. In some embodiments, the biological sample is a plasma sample. In some embodiments, the biological sample is a serum sample. In some embodiments, the biological sample is a urine sample. In some embodiments, the biological sample is a sample of lymphatic fluid. In some embodiments, the sample is a solid tissue sample.

In some embodiments, the method further comprises longitudinally collecting a plurality of biological samples from the transplant recipient, and repeating steps (a) to (d) for each sample collected.

In some embodiments, the quantifying step comprises determining the percentage of donor-derived cell-free DNA out of the total of donor-derived cell-free DNA and recipient-derived cell-free DNA in the blood sample. In some embodiments, the quantifying step comprises determining the number of copies of donor-derived cell-free DNA. In some embodiments, the quantifying step comprises determining the number of copies of donor-derived cell-free DNA per volume unit of the blood sample.

In another aspect, the present invention relates to a method of diagnosing a transplant within a transplant recipient as undergoing acute rejection, comprising: a) isolating cell-free DNA from a biological sample of a transplant recipient, wherein the isolated cell-free DNA comprises donor-derived cell-free DNA and recipient-derived cell-free DNA, wherein a first Tracer DNA composition is added before or after isolation of the cell-free DNA; b) performing targeted amplification at 100 or more different target loci in a single reaction volume using 100 or more different primer pairs; c) sequencing the amplification products by high-throughput sequencing to generate sequencing reads; d) quantifying the amount of donor-derived cell-free DNA and the amount of total cell-free DNA, wherein the amount of donor-derived cell-free DNA above a threshold value indicates that the transplant is undergoing acute rejection, wherein the threshold value is determined according to the amount of total cell-free DNA, and wherein the amount of total cell-free DNA is quantified using sequencing reads derived from the first Tracer DNA composition.

In another aspect, the present invention relates to a method of monitoring immunosuppressive therapy in a transplant recipient, comprising: a) isolating cell-free DNA from a biological sample of a transplant recipient, wherein the isolated cell-free DNA comprises donor-derived cell-free DNA and recipient-derived cell-free DNA, wherein a first Tracer DNA composition is added before or after isolation of the cell-free DNA; b) performing targeted amplification at 100 or more different target loci in a single reaction volume using 100 or more different primer pairs; c) sequencing the amplification products by high-throughput sequencing to generate sequencing reads; d) quantifying the amount of donor-derived cell-free DNA and the amount of total cell-free DNA, wherein a change in levels of donor-derived cell-free DNA over a time interval is indicative of transplant status, wherein the levels of donor-derived cell-free DNA is scaled according to the amount of total cell-free DNA, and wherein the amount of total cell-free DNA is quantified using sequencing reads derived from the first Tracer DNA composition.

In some embodiments, the method further comprises adjusting immunosuppressive therapy based on the levels of dd-cfDNA over the time interval.

In some embodiments, an increase in the levels of dd-cfDNA is indicative of transplant rejection and a need for adjusting immunosuppressive therapy. In some embodiments, no change or a decrease in the levels of dd-cfDNA indicates transplant tolerance or stability, and a need for adjusting immunosuppressive therapy.

In some embodiments, the method further comprises size selection to enrich for donor-derived cell-free DNA and reduce the amount of recipient-derived cell-free DNA disposed from bursting white-blood cells.

In some embodiments, the method further comprises a universal amplification step that preferentially amplifies donor-derived cell-free DNA over recipient-derived cell-free DNA originating from bursting or apoptosing white-blood cells.

In some embodiments, the method comprises longitudinally collecting a plurality of blood, plasma, serum, solid tissue, or urine samples from the transplant recipient after transplantation, and repeating steps (a) to (d) for each sample collected. In some embodiments, the method comprises collecting and analyzing blood, plasma, serum, solid tissue, or urine samples from the transplant recipient for a time period of about three months, or about six months, or about twelve months, or about eighteen months, or about twenty-four months, etc. In some embodiments, the method comprises collecting blood, plasma, serum, solid tissue, or urine samples from the transplant recipient at an interval of about one week, or about two weeks, or about three weeks, or about one month, or about two months, or about three months, etc.

In some embodiments, the determination that the amount of dd-cfDNA above a cutoff threshold is indicative of acute rejection of the transplant. Machine learning may be used to resolve rejection vs non-rejection. Machine learning is disclosed in WO2020/018522, titled "Methods and Systems for calling Ploidy States using a Neural Network" and filed on Jul. 16, 2019 as PCT/US2019/041981, which is incorporated herein by reference in its entirety. In some embodiments, the cutoff threshold value is scaled according to the amount of total cfDNA in the blood sample.

In some embodiments, the cutoff threshold value is expressed as percentage of dd-cfDNA (dd-cfDNA %) in the blood sample. In some embodiments, the cutoff threshold value is expressed as quantity or absolute quantity of dd-cfDNA. In some embodiments, the cutoff threshold value is expressed as quantity or absolute quantity of dd-cfDNA per volume unit of the blood sample. In some embodiments, the cutoff threshold value is expressed as quantity or absolute quantity of dd-cfDNA per volume unit of the blood sample multiplied by body mass, BMI, or blood volume of the transplant recipient.

In some embodiments, the cutoff threshold value takes into account the body mass, BMI, or blood volume of the patient. In some embodiments, the cutoff threshold value takes into account one or more of the following: donor genome copies per volume of plasma, cell-free DNA yield per volume of plasma, donor height, donor weight, donor age, donor gender, donor ethnicity, donor organ mass, donor organ, live vs deceased donor, the donor's familial relationship to the recipient (or lack thereof), recipient height, recipient weight, recipient age, recipient gender, recipient ethnicity, creatinine, eGFR (estimated glomerular filtration rate), cfDNA methylation, DSA (donor-specific antibodies), KDPI (kidney donor profile index), medications (immunosuppression, steroids, blood thinners, etc.), infections (BKV, EBV, CMV, UTI), recipient and/or donor HLA alleles or epitope mismatches, Banff classification of renal allograft pathology, and for-cause vs surveillance or protocol biopsy.

In some embodiments, the method has a sensitivity of at least 50% in identifying acute rejection (AR) over non-AR when the dd-cfDNA amount is above the cutoff threshold value scaled or adjusted according to the amount of total cfDNA in the blood sample and a confidence interval of 95%. In some embodiments, the method has a sensitivity of at least 60% in identifying acute rejection (AR) over non-AR when the dd-cfDNA amount is above the cutoff threshold value scaled or adjusted according to the amount of total cfDNA in the blood sample and a confidence interval of 95%. In some embodiments, the method has a sensitivity of at least 70% in identifying acute rejection (AR) over non-AR when the dd-cfDNA amount is above the cutoff threshold value scaled or adjusted according to the amount of total cfDNA in the blood sample and a confidence interval of 95%. In some embodiments, the method has a sensitivity of at least 80% in identifying acute rejection (AR) over non-AR when the dd-cfDNA amount is above the cutoff threshold value scaled or adjusted according to the amount of total cfDNA in the blood sample and a confidence interval of 95%. In some embodiments, the method has a sensitivity of at least 85% in identifying acute rejection (AR) over non-AR when the dd-cfDNA amount is above the cutoff threshold value scaled or adjusted according to the amount of total cfDNA in the blood sample and a confidence interval of 95%. In some embodiments, the method has a sensitivity of at least 90% in identifying acute rejection (AR) over non-AR when the dd-cfDNA amount is above the cutoff threshold value scaled or adjusted according to the amount of total cfDNA in the blood sample and a confidence interval of 95%. In some embodiments, the method has a sensitivity of at least 95% in identifying acute rejection (AR) over non-AR when the dd-cfDNA amount is be above the cutoff threshold value scaled or adjusted according to the amount of total cfDNA in the blood sample and a confidence interval of 95%.

In some embodiments, the method has a specificity of at least 50% in identifying acute rejection (AR) over non-AR when the dd-cfDNA amount is above the cutoff threshold value scaled or adjusted according to the amount of total cfDNA in the blood sample and a confidence interval of 95%. In some embodiments, the method has a specificity of at least 60% in identifying acute rejection (AR) over non-AR when the dd-cfDNA amount is above the cutoff threshold value scaled or adjusted according to the amount of total cfDNA in the blood sample and a confidence interval of 95%. In some embodiments, the method has a specificity of at least 70% in identifying acute rejection (AR) over non-AR when the dd-cfDNA amount is above the cutoff threshold value scaled or adjusted according to the amount of total cfDNA in the blood sample and a confidence interval of 95%. In some embodiments, the method has a specificity of at least 75% in identifying acute rejection (AR) over non-AR when the dd-cfDNA amount is above the cutoff threshold value scaled or adjusted according to the amount of total cfDNA in the blood sample and a confidence interval of 95%. In some embodiments, the method has a specificity of at least 80% in identifying acute rejection (AR) over non-AR when the dd-cfDNA amount is above the cutoff threshold value scaled or adjusted according to the amount of total cfDNA in the blood sample and a confidence interval of 95%. In some embodiments, the method has a specificity of at least 85% in identifying acute rejection (AR) over non-AR when the dd-cfDNA amount is above the cutoff threshold value scaled or adjusted according to the amount of total cfDNA in the blood sample and a confidence interval of 95%. In some embodiments, the method has a specificity of at least 90% in identifying acute rejection (AR) over non-AR when the dd-cfDNA amount is above the cutoff threshold value scaled or adjusted according to the amount of total cfDNA in the blood sample and a confidence interval of 95%. In some embodiments, the method has a specificity of at least 95% in identifying acute rejection (AR) over non-AR when the dd-cfDNA amount is above the cutoff threshold value scaled or adjusted according to the amount of total cfDNA in the blood sample and a confidence interval of 95%.

Adjusting Threshold for Calling Transplant Rejection Using Amount of Total Cell-Free DNA Some embodiments of the present invention relate to a method of quantifying the amount of donor-derived cell-free DNA in a biological sample of a transplant recipient, comprising: a) isolating cell-free DNA from the biological sample of the transplant recipient, wherein the isolated cell-free DNA comprises donor-derived cell-free DNA and recipient-derived cell-free DNA, wherein a first Tracer DNA composition is added before or after isolation of the cell-free DNA; b) performing targeted amplification at 100 or more different target loci in a single reaction volume using 100 or more different primer pairs; c) sequencing the amplification products by high-throughput sequencing to generate sequencing reads; and d) quantifying the amount of donor-derived cell-free DNA and the amount of total cell-free DNA, wherein the amount of total cell-free DNA is quantified using sequencing reads derived from the first Tracer DNA composition.

Some embodiments use either a fixed threshold of donor DNA per plasma volume or one that is not fixed, such as adjusted or scaled as noted herein. The way that this is determined can be based on using a training data set to build an algorithm to maximize performance. It may also take into account other data such as patient weight, age, or other clinical factors.

In some embodiments, the method further comprises determining the occurrence or likely occurrence of transplant rejection using the amount of donor-derived cell-free DNA. In some embodiments, the amount of donor-derived cell-free DNA is compared to a cutoff threshold value to determine the occurrence or likely occurrence of transplant rejection, wherein the cutoff threshold value is adjusted or scaled according to the amount of total cell-free DNA. In some embodiments, the cutoff threshold value is a function of the number of reads of the donor-derived cell-free DNA.

In some embodiments, the method comprises applying a scaled or dynamic threshold metric that takes into account the amount of total cfDNA in the samples to more accurately assess transplant rejection. In some embodiments, the method further comprises flagging the sample if the amount of total cell-free DNA is above a pre-determined value. In some embodiments, the method further comprises flagging the sample if the amount of total cell-free DNA is below a pre-determined value.

WORKING EXAMPLES

Example 1

The workflow of this non-limiting example corresponds to the workflow disclosed in Sigdel et al., J. Clin. Med. 8(1):19 (2019), which is incorporated herein by reference in its entirety. This example is illustrative only, and a skilled artisan will appreciate that the invention disclosed herein can be practiced in a variety of other ways.

Blood Samples

Male and female adult or young-adult patients received a kidney from related or unrelated living donors, or unrelated deceased donors. Time points of patient blood draw following transplantation surgery were either at the time of an allograft biopsy or at various pre-specified time intervals based on lab protocols. Typically, samples were biopsy-matched and had blood drawn at the time of clinical dysfunction and biopsy or at the time of protocol biopsy (at which time most patients did not have clinical dysfunction). In addition, some patients had serial post transplantation blood drawn. The selection of study samples was based on (a) adequate plasma being available, and (b) if the sample was associated with biopsy information. Among the full 300 sample cohort, 72.3% were drawn on the day of biopsy.

dd-cfDNA Measurement in Blood Samples

Cell-free DNA was extracted from plasma samples using the QIAamp Circulating Nucleic Acid Kit (Qiagen) and quantified on the LabChip NGS 5k kit (Perkin Elmer, Waltham, MA, USA) following manufacturer's instructions. Cell-free DNA was input into library preparation using the Natera Library Prep kit as described in Abbosh et al, *Nature* 545: 446-451 (2017), with a modification of 18 cycles of library amplification to plateau the libraries. Purified libraries were quantified using LabChip NGS 5k as described in Abbosh et al, *Nature* 545: 446-451 (2017). Target enrichment was accomplished using massively multiplexed-PCR (mmPCR) using a modified version of a described in Zimmermann et al., *Prenat. Diagn.* 32:1233-1241 (2012), with 13,392 single nucleotide polymorphisms (SNPs) targeted. Amplicons were then sequenced on an Illumina HiSeq 2500 Rapid Run®, 50 cycles single end, with 10-11 million reads per sample.

Statistical Analyses of dd-cfDNA and eGFR

In each sample, dd-cfDNA was measured and correlated with rejection status, and results were compared with eGFR. Where applicable, all statistical tests were two sided. Significance was set at $p<0.05$. Because the distribution of dd-cfDNA in patients was severely skewed among the groups, data were analyzed using a Kruskal-Wallis rank sum test followed by Dunn multiple comparison tests with Holm correction. eGFR (serum creatinine in mg/dL) was calculated as described previously for adult and pediatric patients. Briefly, $\text{eGFR}=186\times\text{Serum Creatinine}^{-1.154}\times\text{Age}^{-0.203}\times(1.210 \text{ if Black})\times(0.742 \text{ if Female})$.

To evaluate the performance of dd-cfDNA and eGFR (mL/min/1.73 $m^2$) as rejection markers, samples were separated into an AR group and a non-rejection group (BL+STA+OI). Using this categorization, the following predetermined cut-offs were used to classify a sample as AR: >1% for dd-cfDNA and <60.0 for eGFR.

To calculate the performance parameters of each marker (sensitivity, specificity, positive predictive value (PPV), negative predictive value (NPV), and area under the curve (AUC)), a bootstrap method was used to account for repeated measurements within a patient. Briefly, at each bootstrap step, a single sample was selected from each patient; by assuming independence among patients, the performance parameters and their standard errors were calculated. This was repeated 10,000 times; final confidence intervals were calculated using the bootstrap mean for the parameter with the average of the bootstrap standard errors with standard normal quantiles. Standard errors for sensitivity and specificity were calculated assuming a binomial distribution; for PPV and NPV a normal approximation was used; and for AUC the DeLong method was used. Performance was calculated for all samples with a matched biopsy, including the sub-cohort consisting of samples drawn at the same time as a protocol biopsy.

Differences in dd-cfDNA levels by donor type (living related, living non-related, and deceased non-related) were also evaluated. Significance was determined using the Kruskal-Wallis rank sum test as described above. Inter- and intra-variability in dd-cfDNA over time was evaluated using a mixed effects model with a logarithmic transformation on dd-cfDNA; 95% confidence intervals (CI) for the intra- and inter-patient standard deviations were calculated using a likelihood profile method.

Post hoc analyses evaluated (a) different dd-cfDNA thresholds to maximize NPV and (b) combined dd-cfDNA and eGFR to define an empirical rejection zone that may improve the PPV for AR diagnosis. All analyses were done using R 3.3.2 using the FSA (for Dunn tests), Ime4 (for mixed effect modeling) and pROC (for AUC calculations) packages.

Biopsy Samples

Optionally, kidney biopsies were analyzed in a blinded manner by a pathologist and were graded by the 2017 Banff classification for active rejection (AR); intragraft C4d stains were performed to assess for acute humoral rejection. Biopsies were not done in cases of active urinary tract infection (UTI) or other infections. Transplant "injury" was defined as a >20% increase in serum creatinine from its previous steady-state baseline value and an associated biopsy that was classified as either active rejection (AR), borderline rejection (BL), or other injury (OI) (e.g., drug toxicity, viral infection). Active rejection was defined, at minimum, by the following criteria: (1) T-cell-mediated rejection (TCMR) consisting of either a tubulitis (t) score>2 accompanied by an interstitial inflammation (i) score>2 or vascular changes (v) score>0; (2) C4d positive antibody-mediated rejection (ABMR) consisting of positive donor specific antibodies (DSA) with a glomerulitis (g) score>0/or peritubular capillaritis score (ptc)>0 or v>0 with unexplained acute tubular necrosis/thrombotic micro angiopathy (ATN/TMA) with C4d=2; or (3) C4d negative ABMR consisting of positive DSA with unexplained ATN/TMA with g+ptc≥2 and C4d is either 0 or 1. Borderline change (BL) was defined by t1+10, or t1+i1, or t2+i0 without explained cause (e.g., polyomavirus-associated nephropathy (PVAN)/infectious cause/ATN). Other criteria used for BL changes were g>0 and/or ptc>0, or v>0 without DSA, or C4d or positive DSA, or positive C4d without nonzero g or ptc scores. Normal (STA) allografts were defined by an absence of significant injury pathology as defined by Banff schema.

Example 2

This example is illustrative only, and a skilled artisan will appreciate that the invention disclosed herein can be practiced in a variety of other ways. The workflow described in Example 1 is modified by adding one or more Tracer DNA(s) each containing a SNP locus to the plasma sample prior to extraction of cell-free DNA, as described in U.S. Prov. Appl. No. 63/031,879 filed May 29, 2020 and titled "Improved Methods for Detection of Donor Derived Cell-Free DNA", which is incorporated herein by reference in its entirety. During the mmPCR target enrichment step, the primer pairs targeting the SNP locus also amplify the Tracer DNA(s). The amount of total cfDNA in the sample is estimated using the number of sequences reads of the Tracer DNA(s) which are identifiable by the barcode, the number of sequences reads of sample DNA, and the known amount of the Tracer DNA(s) added to the plasma sample.

Example 3

*Torque teno* virus (TTV), a non-pathogenic and ubiquitous virus, is associated with immunosuppression and graft rejection in solid organ transplant recipients. We quantified plasma TTV titer copies/mL (cps/mL) in kidney transplant recipients (n=687) and healthy, normal controls (n=56). TTV titer drastically increased by approximately 4 log-fold during the first 3 months post-transplantation, before decreasing slightly and stabilizing over time. Lower TTV levels significantly correspond to high risk of allograft rejection (median 7.49E+04 as compared to low risk rejection (median 7.70E+05) (p<0.001). Logistic regression analysis of a subgroup of transplant samples with biopsy rejection data that were ≤18 months post-transplantation (n=82), revealed that the area under the curve (AUC) increased to AUC=0.89, when we combined TTV titer to donor fraction estimate (DFE)-plus donor-derived cell-free DNA, time post-transplantation, age and gender (DFE+), compared to DFE+ alone (AUC=0.87), or TTV alone (AUC=0.72). Addition of TTV increased sensitivity (0.84, 95% CI [0.64, 0.95] vs 0.80, 95% CI [0.59, 0.93]) and specificity (0.86, 95% CI [0.74, 0.94] vs 0.82, 95% CI [0.70, 0.91]), when compared to DFE+ in the ≤18 months post-transplant subgroup. Overall, these results suggest that TTV is a non-invasive biomarker associated with immunosuppression and allograft rejection.

Background Transplant physicians still face challenges in assessing the net state of immunosuppression of their patients, which results from the complex interaction among pre-transplant conditions, induction and maintenance immunosuppressive regimens, graft function, anti-rejection therapies, nutritional state and underlying comorbidities. Therapeutic drug monitoring of immunosuppressive agents appears as the most widely used strategy in current clinical practice. However, this approach is strictly pharmacokinetic in nature and does not capture the inter-individual variability in T cell responses at given concentrations, or the synergistic effect of combination immunosuppressive regimens. The development of noninvasive biomarkers that reflect the state of immunosuppression remains an unmet need in transplantation to adjust maintenance immunosuppression in solid organ transplant recipients.

TTV is a highly prevalent, non-pathogenic single-strand DNA virus whose plasma levels may be associated with the immune status of the host. Several studies report a significant increase of TTV plasma DNA levels in allogeneic transplant recipients and suggest a correlation of elevated virus titers with immunosuppression and transplant-related complications like rejection. Therefore, our primary objective was to determine whether TTV titer is associated with immunosuppression and kidney transplant rejection risk.

Methods

Patient samples. Kidney transplant recipient plasma or cfDNA samples (n=687 from Prospera tests were used to screen for TTV. Healthy human plasma was purchased from Innovative Research. All samples were from clinics based in the USA and patients provided consent for research use. The range of time post-transplantation was 10 days-40 years, with a median of 9 months. Total cfDNA, donor status, donor relationship, gender, and donor fraction estimate were known. In a subgroup of samples, we also had histological, biopsy-proven graft rejection status with clinical interpretation, according to BANFF classification.

Extraction of nucleic acids from plasma. Two methods of nucleic acid extraction were used to extract DNA and RNA from human plasma. First, we used the MagMAX™ Viral/Pathogen Nucleic Acid Isolation Kit (ThermoFisherScientific Cat #A42352) to isolate DNA and RNA from 300 µl plasma according to the manufacturer's manual and automated the protocol on the KingFisher Flex extraction instrument (ThermoFisherScientific). In brief, 10 µl Proteinase K. 530 µl Binding Solution, and 20 µl Total Nucleic Acid Magnetic Beads were added to 300 µl plasma, incubated for 12 minutes, bead wash with Wash Buffer and 80% ethanol, and eluted the nucleic acid in 50 µl Elution Solution. The second nucleic acid isolation method was Natera's In-House Extraction method.

TTV primer, probe, and reference design. To quantify TTV DNA, we developed a TTV quantitative PCR (qPCR) assay with a primer and probe set based on the design by Okamoto, Hiroaki et. al. "Heterogeneous distribution of TT virus of distinct genotypes in multiple tissues from infected humans." *Virology* 288.2 (2001): 358-368. The primers and probe were designed on the well-conserved region of the 5'-UTR (nucleotide position 3075-3853 and 1-352) of the complete genome of TTV virus genotype 1a (GenBank: AB017610.1) (Table 1). Analysis of the primers in the genome database, NCBI RefSeq, reveal that these TTV primers are estimated to cover 93% of Anelloviridae strains.

In the Okamoto et al. paper, the forward and reverse primers have two incompletely specified bases (Table 1). The Okamoto forward primer has the symbol, "D." which can be A, G. or T and the reverse primer has the symbol, "R." which can be A or G. We substituted both those symbols with nucleotide "A" to match the sequence of TTV virus genotype 1a. In addition, for the probe, we switched the single TAMRA quencher to a double quenched probe of ZEN/Iowa Black FQ® (3' IABKFQ) for reduced background and superior performance compared to single-quenched probes (Table 1).

Commercial TTV reference DNA was unavailable at time of performing this experiment. In vitro transcription of TTV has been investigated in a variety of cell lines and long-term replication leading to virus production has been difficult to achieve. Academic labs have amplified the TTV genome by cloning the sequence into vectors, but these were unavailable for industry-use at time of experiment. Therefore, an equal conserved sequence of the 5' UTR was designed to serve as a reference standard for the TTV qPCR assay covering approximately 83% of the different TTV substrains. This 500 bp gBlock includes the nucleotide position that matches the primers and probes (Table 1). Primers, probe, and gBlock were manufactured by IDT.

TABLE 1

TTV qPCR primers, probe, and reference qBlock sequence

| | Sequence (5'-3') | Nucleotide position | Length (bp) | Amplicon length (bp) |
|---|---|---|---|---|
| TTV-Fwd primer | CGG GTG CCG **A**AG GTG AGT TTA CAC | 174-197 | 24 | 32 |
| Okamoto Fwd primer (NG473) | CGG GTG CCG **D**AG GTG AGT TTA CAC<br>D = A, G, or T | | | |
| TTV-Rev primer | GAG CCT TGC CCA T**A**G CCC GGC CAG | 229-252 | 24 | |
| Okamoto Rev primer (NG352) | GAG CCT TGC CCA T**R**G CCC GGC CAG<br>R = A or G | | | |
| TTV-Probe | 6-<br>FAM/AGTCAAGGG/ZEN/GCAATTCGGGCTC<br>GGGA/IABKFQ | 204-230 | 26 | — |
| Okamoto Probe | 6-<br>FAM/AGTCAAGGGGCAATTCGGGCTCGGG<br>A/TAMRA | | | |
| TTV gBlock reference | ATTTTGCTACGTCACTAACCACGTGACACC<br>CACAGGCCAACCGAATGCTATGTCATCCAT<br>TTCCTGGGCCGGGTCTACGTCCTCATATAA<br>GTAAGTGCACTTCCGAATGGCTGAGTTTTC<br>CACGCCCGTCCGCAGCGGTGAAGCCACGG<br>AGGGAGATCTCCGCGTCCCGAGGGCGGGT<br>GCCGAAGGTGAGTTTACACACCGAAGTCA<br>AGGGGCAATTCGGGCTCGGGACTGGCCGG<br>GCTATGGGCAAGGCTCTGAAAAAAGCATG<br>TTTATTGGCAGGCATTACAGAAAGAAAAG<br>GGCGCTGTCACTGTGTGCTGTGCGAACAAC<br>AAAGAAGGCTTGCAAACTACTAATAGTAA<br>TGTGGACCCCACCTCGCAATGATCAACACT<br>ACCTTAACTGGCAATGGTACTCAAGTATAC<br>TTAGCTCCCACGCTGCTATGTGCGGGTGTC<br>CCGACGCTGTCGCTCATTTTAATCATCTTG<br>CTTCTGTGCTTCGTGCCCCGCAAAACC | 1-500 | 500 | — |

TTV quantitation. TTV DNA was quantified by qPCR using 5 μl nucleic acid solution as a template, 400 nM Forward/Reverse primer, 80 nM probe, TaqMan™ Fast Advanced Master Mix (ThermoFisherScientific Cat. #4444964), molecular-grade water, and spiked-in with TaqMan™ Exogenous Internal Positive Control (IPC) Reagents (ThermoFisherScientific Cat. #4308321) in a 25 μl reaction volume. qPCR cycling conditions are 1) uracil-DNA glycosylases (UNG) activation at 50° C. hold for 2 minutes, 2) AmpliTaq™ Fast DNA Polymerase activation at 95° C. hold for 2 minutes, and 3) 40 cycles of PCR with Denature step at 95° C. for 1 second and Anneal/Extend step at 60° C. for 20 seconds. All reactions were performed in a QuantStudio6 (ThermoFisherScientific). The fluorescence channels were FAM for the TTV target nucleic acid, VIC for the IPC, NFQ-MGB for the quencher, and ROX for the passive reference present in the TaqMan™ Fast Advanced Master Mix. Each reaction plate was plated with a TTV Reference gBlock standard composed of 1E+07, 1E+06, 1E+05, 1E+04, 1E+03, 1E+02 copies/mL (cps/mL), and three negative controls: molecular grade water, cell line DNA (10 ng/mL), and no amplification control-IPC Block. The TTV qPCR assay has a quantitative detection range of Log 1E+03-1E+10 cps/mL and the theoretical limit of detection (LOD) is 1 copy in a 25 μl PCR reaction, which corresponds to 33 copies present in 300 μl plasma.

Statistics and data analysis. Bivariate analysis of TTV titer over time post-transplantation was plotted to observe viral load kinetics. Regularized logistic regression model was used to estimate the effect size of the association between graft rejection and TTV titer. Several statistical tests (Mann-Whitney, Mantel-Haenszel), threshold based and machine learning models (Decision Tree, Logistic Regression, and Random Forest) were evaluated on a subgroup of the dataset. We used feature importance analysis and sensitivity/specificity comparisons to determine the importance of TTV in predicting the rejection. Various models were employed as orthogonal methods of statistical and machine learning tests. Agreement between tests and models could provide more confidence in our findings. QuantStudio Software v1.7.2, JMP 12, R and Jupyter were applied for data analysis and generation of graphical plots.

Description of multi-parameter AI method. To quantify the additional TTV titer effect on the quality of rejection prediction, machine learning models, which incorporated TTV as a feature, were compared against the ones which did not, given other features unchanged. Other features included DFE, dd-cfDNA quantity, Recipient Age, Recipient Gender, Donor Status, Donor/Recipient Relationship, and Time Post Transplantation. For the Logistic Regression, L2 regularization parameters were derived using cross-validation on the train set. For the Random Forest, a small maximum depth of trees was chosen to avoid overfitting. All the models were evaluated on the test set. We compared the area under the curves (AUCs), sensitivities and specificities for various thresholds between the models above, which either incorporated TTV as a feature or not. We also compared the above results to the threshold-based models, which directly used DFE, dd-cfDNA quantity, and TTV as predictors.

Results

Post-transplant TTV load peaked in first 3 months. We developed a TTV qPCR assay to measure TTV titer copies/mL (cps/mL) in human plasma. We used our TTV qPCR assay to screen kidney transplant recipients (n=68) and healthy, normal control (n=56) plasma samples. Viral nucleic acid from 75% of transplant recipient plasma samples and all controls were extracted using the MagMAX™ Viral/Pathogen Nucleic Acid Isolation Kit. Nucleic acid from the second cohort of biopsy matched samples was extracted using Natera's In-House Extraction method. Plasma was collected between 10 days and 26 years post-transplantation at the time of Prospera and TTV screen. TTV was present in 97% of samples of transplant recipients versus 61% in healthy, normal controls.

Transplant recipients had significantly higher TTV titer levels (range=0-2.24E+10 cps/mL; median=4.25E+05 cps/mL) than normal controls (range=0-1.49E+05 cps/mL; median=3.20E+02 cps/mL) ($p \leq 1.08E-08$) (FIG. 1). Higher TTV titer reflects the fact that most if not all transplant recipients are immunosuppressed. TTV titer drastically increases by approximately 4 log-fold during the first 3 months post-transplantation, before decreasing slightly and stabilizing over time (FIG. 1). This may correspond to induction and then maintenance immunosuppressive therapy regimen.

Figure 2:
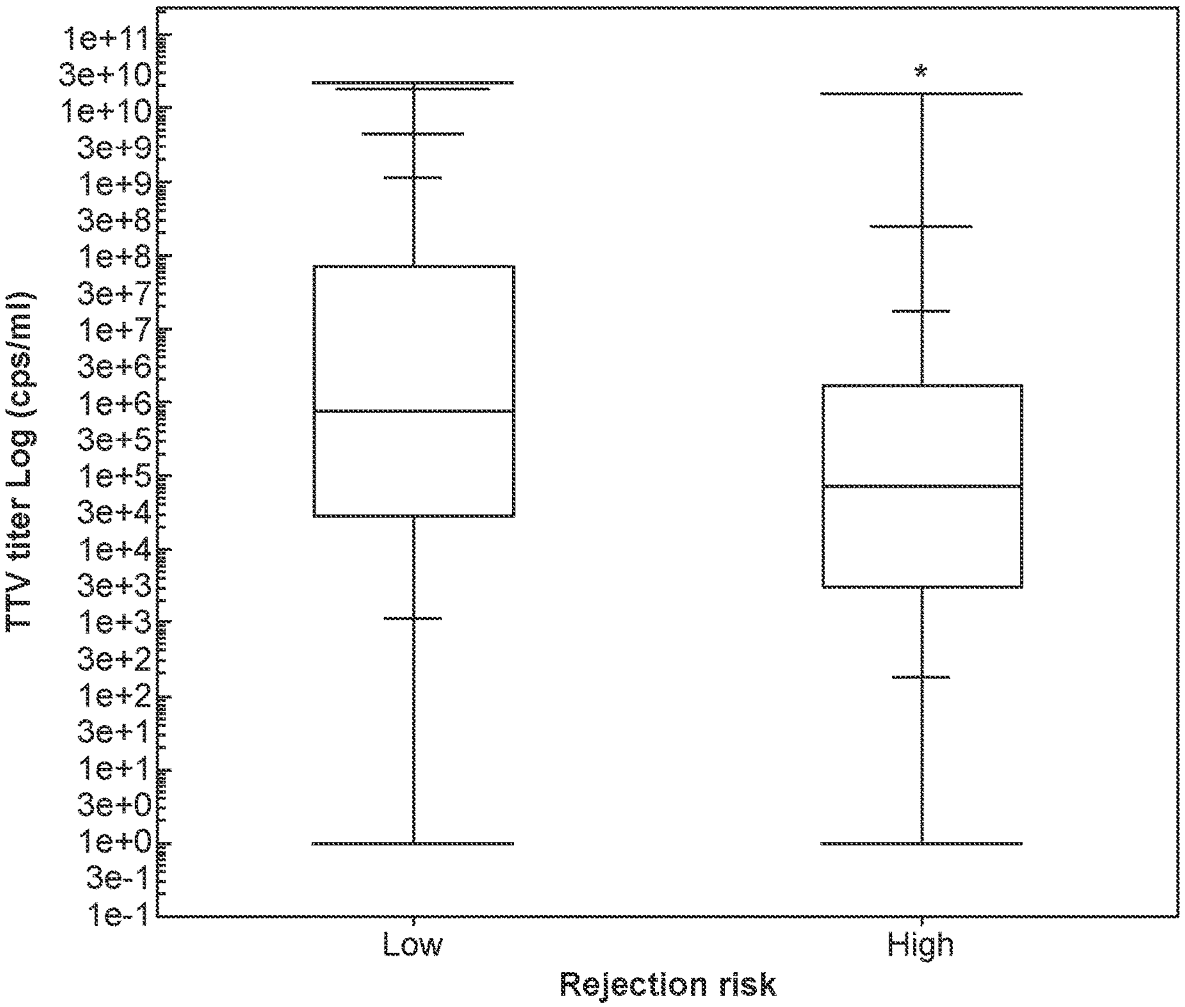
FIG. 2. TTV titer Log (cps/mL) of Low and High graft rejection risk is plotted in box plots. where the box represents the 25th and 75th percentile, and the horizontal line represents the median. The whiskers represent approximately 95% of the data. * $p<0.001$.

Lower TTV levels correspond to high risk of allograft rejection. To determine whether TTV has the potential to predict risk of graft rejection, TTV titer was compared between high or low allograft rejection risk. Rejection risk was determined by DFE from the patient's Prospera results, which is Natera's transplant rejection assessment test that measures donor-derived cell-free DNA (dd-cfDNA). Lower TTV levels significantly correspond to high risk rejection (median 7.49E+04, as compared to low risk rejection (median 7.70E+05 ($p<0.001$) (FIG. 2). High risk of allograft rejection suggests increased immune activity, which coincides with lower TTV load.

TTV offers improvement in Prospera sensitivity and specificity. We aimed to assess if TTV is associated with rejection. If so, we may use this biomarker to improve our Prospera calling with increased sensitivity and specificity. We had biopsy-proven rejection information for a particular subgroup of samples (n=171). These samples were a mix of False Negative (n=20), False Positive (n=21), True Negative (n=84), and True Positive (n=47) samples. Prospera results from this sample set yielded a sensitivity of 70.1%, specificity of 80.0%, PPV of 69.1%, and NPV of 80.8%.

Mann-Whitney and Mantel-Haenszel statistical tests and threshold-based, decision tree, logistic regression, and random forest machine learning tests determined that TTV did not significantly improve sensitivity and/or specificity when analyzing the entire set of samples. We hypothesized that the large range of time post-transplantation of 11 days-25 years added considerable noise to the dataset in regards to TTV titer. Induction therapy and maintenance immunosuppression regimen are at their highest dose in the first 18 months post-transplant. This provides the greatest level of immunosuppression and biggest effect on TTV titer as demonstrated in literature. Therefore, we performed logistic regression and random forest machine learning analysis on a subgroup of samples that were ≤18 months post-transplantation (n=82).

Figure 3:
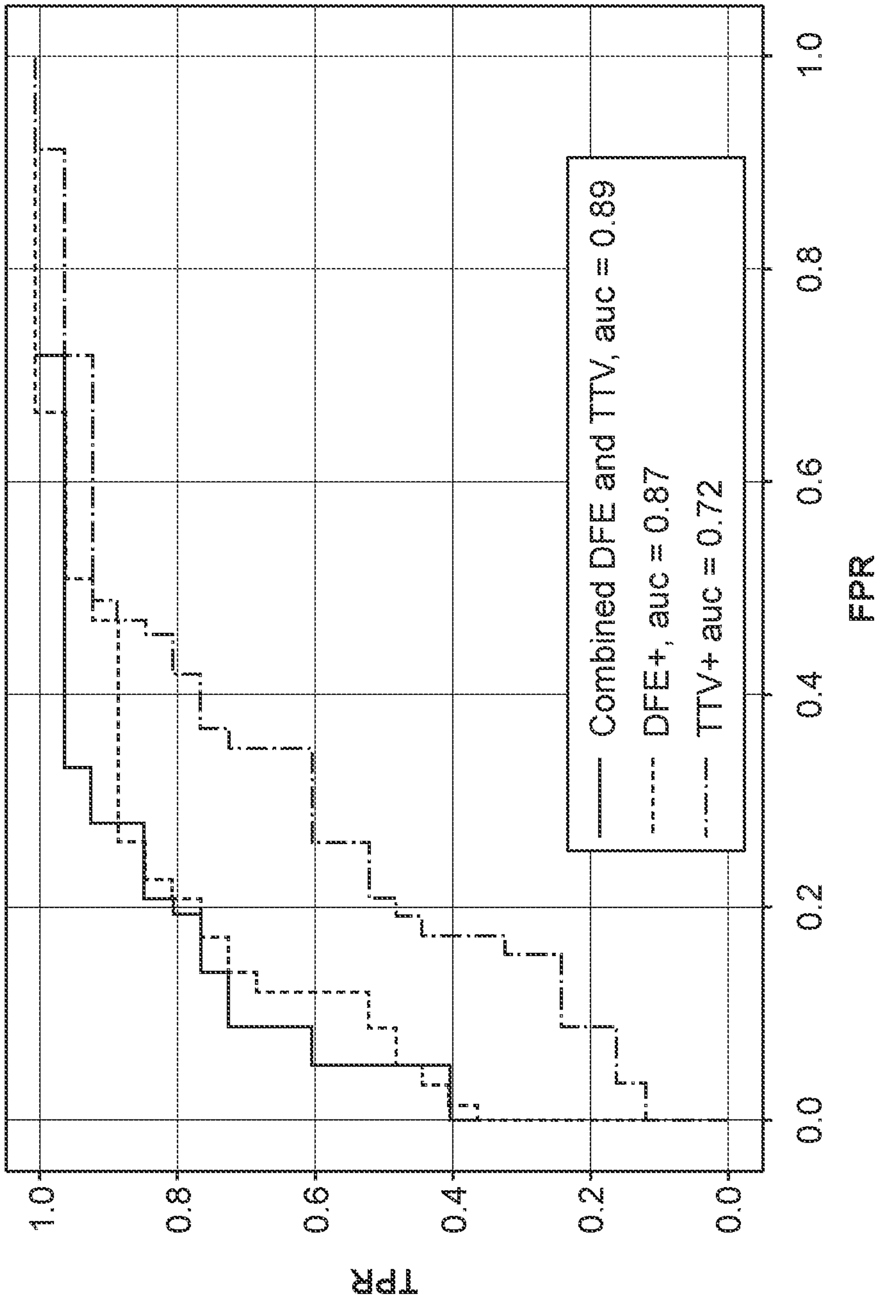
FIG. 3. TTV improves prediction of allograft rejection combined with Prospera (DFE), based on subset of 171 samples, including 67 biopsy confirmed rejections, that were sampled ≤18 months post-transplantation. AUC of TTV+DFE increased by 3% compared to DFE alone. Logistic regression models were used to generate receiver operating characteristic (ROC) curves to assess whether TTV added value to Prospera's donor fraction estimate (DFE) by calculating the area under the curve (AUC). All of the analyses utilized the BANFF-classification for allograft pathology for the Final Call for rejection/non-rejection. TPR: true positive rate, FPR: false positive rate. '+' means the model includes multiple features such as DFE, dd-cfDNA quantity, TTV, time post-transplantation, age, and gender. The train+test sets were included to generate the ROC curves.

In subgroup of samples≤18 months post-transplantation, logistic regression-based receiver operating characteristic (ROC) curves reveal that the AUC increased to AUC=0.89, when we combined TTV titer to DFE+, in comparison to DFE+ alone (AUC=0.87), or TTV alone (AUC=0.72) (FIG. 3). TTV increased sensitivity (0.84, 95% CI [0.64, 0.95] vs 0.80, 95% CI [0.59, 0.93]) and specificity (0.86, 95% CI [0.74, 0.94] vs 0.82, 95% CI [0.70, 0.91]) in the logistic regression-based model, when compared to DFE+ alone. To note, these preliminary results are derived from a small sample set and the confidence intervals are wide due to interpatient variability of TTV titer. Additional studies with longitudinal samples will further quantify the value TTV can add to Prospera.

Summary. The percentage of TTV-positive transplant plasma samples, TTV titer range, and kinetics are in line with literature, which suggests that our TTV qPCR assay is sensitive and robust. We show that lower TTV levels significantly correspond to high risk of allograft rejection. Also, we find that TTV increases Prospera AUC compared to DFE+ alone, with increased sensitivity and specificity, in samples≤18 months post-transplantation. Taken together, our data provides evidence for the value of TTV quantitation as a non-invasive biomarker for immunosuppression and risk stratification of graft rejection in conjunction with Prospera, with greatest utility within 18 months post-transplantation.

The invention claimed is:

1. A method of preparing a composition of amplified DNA derived from a blood, plasma, serum or urine sample of a transplant recipient useful for determination of transplant rejection, comprising:

(a) extracting cell-free DNA from the blood, plasma, serum or urine sample of the transplant recipient, wherein the extracted cell-free DNA comprises donor-derived cell-free DNA and recipient-derived cell-free DNA;
(b) preparing a composition of amplified DNA by performing targeted amplification of the extracted DNA at 200-50,000 target loci in a single reaction volume, and sequencing the amplified DNA by high-throughput sequencing to obtain sequencing reads and quantifying the amount of donor-derived cell-free DNA based on the sequencing reads;
(c) measuring the amount of *Torque teno* virus (TTV) in a blood, plasma, serum, or urine sample of the transplant recipient; and
(d) determining whether the amount of donor-derived cell-free DNA or a function thereof, or the amount of TTV or a function thereof, crosses a cutoff threshold indicating transplant rejection, wherein the blood, plasma, serum or urine sample is obtained from the transplant recipient less than 18 months post-transplantation.

2. A method of preparing a composition of amplified DNA derived from a blood, plasma, serum or urine sample of a transplant recipient useful for determination of transplant rejection, comprising:
(a) extracting cell-free DNA from the blood, plasma, serum or urine sample of the transplant recipient, wherein the extracted cell-free DNA comprises donor-derived cell-free DNA and recipient-derived cell-free DNA;
(b) preparing a composition of amplified DNA by performing targeted amplification of the extracted DNA at 200-50,000 target loci in a single reaction volume, and sequencing the amplified DNA by high-throughput sequencing to obtain sequencing reads and quantifying the amount of donor-derived cell-free DNA and the amount of *Torque teno* virus (TTV) based on the sequencing reads; and
(c) determining whether a combination of the amount of donor-derived cell-free DNA or a function thereof and the amount of TTV or a function thereof exceeds a cutoff threshold indicating transplant rejection,
wherein the blood, plasma, serum or urine sample is obtained from the transplant recipient less than 18 months post-transplantation.

3. The method of claim 1, wherein the TTV is *Torque teno* virus 1.

4. The method of claim 1, wherein the transplant recipient is a human subject.

5. The method of claim 1, wherein the transplant recipient has received one or more transplanted organs selected from pancreas, kidney, liver, heart, lung, intestine, thymus, and uterus.

6. The method of claim 1, wherein the amount of TTV is measured by quantitative PCR, real-time PCR, digital PCR, or sequencing.

7. The method of claim 1, wherein the target loci comprise single nucleotide polymorphisms (SNPs).

8. The method of claim 1, wherein step (b) comprises PCR amplification of 200-50,000 target loci using 200-50,000 pairs of forward and reverse PCR primers; optionally wherein step (b) comprises PCR amplification of 500-20,000 target loci using 500-20,000 pairs of forward and reverse PCR primers.

9. The method of claim 1, wherein the cutoff threshold is an estimated percentage of donor-derived cell-free DNA out of total cell-free DNA or a function thereof.

10. The method of claim 1, wherein the cutoff threshold is proportional to an absolute donor-derived cell-free DNA concentration.

11. A method of administering immunosuppressive therapy in a transplant recipient, comprising:
(a) measuring the amount of *Torque teno* virus (TTV) in a blood, plasma, serum, or urine sample of the transplant recipient;
(b) measuring the amount of donor-derived cell-free DNA in a blood, plasma, serum, or urine sample of the transplant recipient; and
(c) titrating the dosage of an immunosuppressive therapy according to the amount of TTV or a function thereof and the amount of donor-derived cell-free DNA or a function thereof,
wherein the blood, plasma, serum or urine sample is obtained from the transplant recipient less than 18 months post-transplantation.

12. The method of claim 11, further comprising repeating steps (a)-(b) longitudinally for the same transplant recipient, and determining a longitudinal change in the amount of TTV or a function thereof and a longitudinal change in the amount of donor-derived cell-free DNA or a function thereof.

13. The method of claim 12, further comprising titrating the dosage of the immunosuppressive therapy according to the longitudinal change in the amount of TTV or a function thereof and the longitudinal change in the amount of donor-derived cell-free DNA or a function thereof.

14. The method of claim 13, comprising increasing the dosage of immunosuppressive therapy if the transplant recipient has a longitudinally decreased amount of TTV and a longitudinally increased amount of donor-derived cell-free DNA.

15. The method of claim 13, comprising decreasing the dosage of immunosuppressive therapy if the transplant recipient has a longitudinally increased amount of TTV and a longitudinally decreased amount of donor-derived cell-free DNA.

16. The method of claim 1, wherein step (d) further comprises:
(d) determining the rejection risk for the transplant recipient based on the amount of donor-derived cell-free DNA and/or the percentage of donor-derived cell-free DNA out of total cell-free DNA, and the amount of TTV in the blood, plasma, serum, or urine sample of the transplant recipient.

17. The method of claim 16, wherein the rejection risk for the transplant recipient is determined using logistic regression, random forest, or decision tree machine learning analysis.

18. The method of claim 17, wherein the logistic regression, random forest, or decision tree machine learning analysis further incorporates one or more parameters selected from time post-transplantation, age of transplant recipient and/or transplant donor, gender of transplant recipient and/or transplant donor, or the amount of total cell-free DNA in the blood, plasma, serum or urine sample or a function thereof.

* * * * *